(12) United States Patent
Deisseroth et al.

(10) Patent No.: US 10,569,099 B2
(45) Date of Patent: *Feb. 25, 2020

(54) SYSTEM FOR OPTICAL STIMULATION OF TARGET CELLS

(71) Applicant: The Board of Trustees of the Leland Stanford Junior University, Palo Alto, CA (US)

(72) Inventors: Karl Deisseroth, Stanford, CA (US); M. Bret Schneider, Portola Valley, CA (US); David J. Mishelevich, Playa Del Rey, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,305

(22) Filed: Nov. 10, 2014

(65) Prior Publication Data

US 2015/0217128 A1 Aug. 6, 2015

Related U.S. Application Data

(63) Continuation of application No. 11/651,422, filed on Jan. 9, 2007, now Pat. No. 8,926,959, which is a continuation-in-part of application No. 11/459,636, filed on Jul. 24, 2006, now Pat. No. 8,906,360.

(60) Provisional application No. 60/701,799, filed on Jul. 22, 2005.

(51) Int. Cl.
| | |
|---|---|
| *A61N 5/06* | (2006.01) |
| *A61K 48/00* | (2006.01) |
| *A61K 38/17* | (2006.01) |
| *A61K 41/00* | (2020.01) |

(52) U.S. Cl.
CPC ............ *A61N 5/062* (2013.01); *A61K 38/177* (2013.01); *A61K 41/0057* (2013.01); *A61K 48/005* (2013.01); *A61K 48/0058* (2013.01); *A61K 48/0075* (2013.01); *A61K 48/0083* (2013.01); *A61N 5/0601* (2013.01); *A61N 5/0622* (2013.01); *A61N 2005/0651* (2013.01); *Y10S 530/825* (2013.01)

(58) Field of Classification Search
CPC .... A61N 5/062; A61N 5/0601; A61N 5/0622; A61N 2005/0651; A61K 38/177; A61K 48/005; A61K 48/0058; A61K 48/0075; A61K 48/0083; Y10S 530/825
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Knox et al. "Heterologous expression of limulus rhodopsin." J Biol Chem. Oct. 17, 2003;278(42):40493-502 (Year: 2003).*
Boyden E. "A history of optogenetics: the development of tools for controlling brain circuits with light." F1000 Biol Rep. 2011;3:11. (Year: 2011).*
Zhang et al. "The Microbial Opsin Family of Optogenetic Tools." Cell. Dec. 23, 2011;147(7):1446-1457 (Year: 2011).*
Rein et al. "The optogenetic (r)evolution." Mol Genet Genomics (2012) 287:95-109 (Year: 2012).*
Lin et al. "Characterization of Engineered Channelrhodopsin Variants with Improved Properties and Kinetics." Biophys J. Mar. 4, 2009; 96(5): 1803-1814. (Year: 2009).*

(Continued)

*Primary Examiner* — Titilayo Moloye
(74) *Attorney, Agent, or Firm* — Rudy J. Ng; Paula A. Borden; Bozicevic, Field & Francis LLP

(57) ABSTRACT

Stimulation of target cells using light, e.g., in vivo, is implemented using a variety of methods and devices. According to an example embodiment of the present invention, target cells are stimulated using an implantable arrangement. The arrangement includes an electrical light-generation means for generating light and a biological portion. The biological portion has a photosensitive biomolecular arrangement that responds to the generated light by stimulating target cells in vivo.

13 Claims, 12 Drawing Sheets

(56) References Cited

U.S. PATENT DOCUMENTS

| | | |
|---|---|---|
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 * | 2/2002 | Alfano ............... C12N 15/87 128/898 |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,249,234 B2 | 2/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 * | 2/2003 | Miesenbock .... C07K 14/43581 435/69.1 |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 * | 1/2004 | Monahan ............... A61K 48/00 424/93.2 |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 * | 4/2004 | Pachys ................. A61N 5/0601 607/88 |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0107753 A1 * | 5/2005 | Rezai ................ A61M 5/14276 604/288.04 |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 * | 9/2005 | Hegemann ............. A61K 38/16 435/4 |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |

(56) References Cited

U.S. PATENT DOCUMENTS

| | | |
|---|---|---|
| 2005/0267454 A1 | 12/2005 | Hissong et al. |
| 2005/0279354 A1* | 12/2005 | Deutsch ............. A61B 1/07 128/200.24 |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0131837 A1 | 10/2009 | Zhang et al. |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0224095 A1 | 9/2011 | Zoller et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0089503 A1 | 4/2013 | Deisseroth et al. |
| 2013/0090454 A1 | 4/2013 | Deisseroth et al. |
| 2013/0144359 A1 | 6/2013 | Kishawi et al. |
| 2013/0184817 A1 | 7/2013 | Deisseroth et al. |
| 2013/0224821 A1 | 8/2013 | Deisseroth et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0289676 A1 | 10/2013 | Deisseroth et al. |
| 2013/0295015 A1 | 11/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0331441 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0024701 A1 | 1/2014 | Deisseroth et al. |
| 2014/0082758 A1 | 3/2014 | Deisseroth et al. |
| 2014/0113367 A1 | 4/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0309705 A1 | 10/2014 | Deisseroth et al. |
| 2014/0323849 A1 | 10/2014 | Deisseroth et al. |
| 2014/0324133 A1 | 10/2014 | Deisseroth et al. |
| 2015/0112411 A1 | 4/2015 | Beckman et al. |

FOREIGN PATENT DOCUMENTS

| | | |
|---|---|---|
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |

(56) References Cited

FOREIGN PATENT DOCUMENTS

| | | |
|---|---|---|
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2013/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (dated May 9, 2012).
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No. 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs";

(56) References Cited

OTHER PUBLICATIONS 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).

Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Adamantidis et al., "Optogenetic Interrogation of Dopaminergic Modulation of the Multiple Phases of Reward-Seeking Behavior", J. Neurosci (2011), 31(30):10829-35.
Aebischer et al., "Long-Term Cross-Species Brain Transplantation of a Polymer-Encapsulated Dopamine-Secreting Cell Line", Experimental Neurology (1991), 111:269-275.
Ahmad et al., "The *Drosophila rhodopsin* cytoplasmic tail domain is required for maintenance of rhabdomere structure", The FASEB Journal (2007), 21:449-455.
Airan et al., "Temporally Precise in vivo Control of Intracellular Signaling", Nature (2009), 458(7241):1025-1029.
Akirav et al., "The role of the medial prefrontal cortex-amygdala circuit in stress effects on the extinction of fear", Neural Plasticity (2007), 2007:Article ID 30873.
Ang et at., "Hippocampal CA1 Circuitry Dynamically Gates Direct Cortical Inputs Preferentially at Theta Frequencies", The Journal of Neurosurgery (2005), 25(42):9567-9580.
Araki et al., "Site-Directed Integration of the cre Gene Mediated by Cre Recombinase Using a Combination of Mutant lox Sites", Nucleic Acids Research (2002), 30(19):1-8.

(56) References Cited

OTHER PUBLICATIONS

Aravanis et al., "An optical neural interface: in vivo control of rodent motor cortex with integrated fiberoptic and optogenetic technology", J. Neural. Eng. (2007), 4(3):S143-S156.
Arenkiel et al., "In vivo light-induced activation of neural circuitry in transgenic mice expressing Channelrhodopsin-2", Neuron (2007), 54:205-218.
Argos et al., "The integrase family of site-specific recombinases: regional similarities and global diversity", The EMBO Journal (1986), 5(2):433-440.
Balint et al., "The Nitrate Transporting Photochemical Reaction Cycle of the Pharanois Halorhodopsin", Biophysical Journal, 2004, 86:1655-1663.
Bamberg et al., "Light-driven proton or chloride pumping by halorhodopsin", Proc. Natl. Academy Science USA (1993), 90(2):639-643.
Banghart et al., "Light-activated ion channels for remote control of neuronal firing", Nature Neuroscience (2004), 7(12):1381-1386.
Basil et al., "Is There Evidence for Effectiveness of Transcranial Magnetic Stimulation in the Treatment of Psychiatric Disorders?" Psychiatry (2005), 2(11):64-69.
Bebbington et al., "The use of vectors based on gene amplification for the expression of cloned genes in mammalian cells" in "DNA cloning vol. 3", Academic Press, New York (2007).
Benabid, "Future strategies to restore brain functions," Conference proceedings from Medicine Meets Millennium: World Congress of Medicine and Health (2000), 6 pages.
Benoist et al., "In vivo sequence requirements of the SV40 early promoter region", Nature (1981), 290(5804):304-310.
Berges et al., "Transduction of Brain by Herpes Simplex Virus Vectors", Molecular Therapy (2007), 15(1):20-29.
Berke et al., "Addiction, Dopamine, and the Molecular Mechanisms of Memory", Molecular Plasticity (2000), 25:515-532.
Berndt et al., "Bi-stable neural state switches", Nature Neuroscience (2009), 12(2):229-234.
Berndt et al., "Structure-guided transformation of channelrhodopsin into a light-activated chloride channel", Science (2014), 344:420-424.
Berridge et al., "The Versatility and Universality of Calcium Signaling", Nature Reviews: Molecular Cell Biology (2000), 1:11-21.
Bocquet et al., "A prokaryotic proton-gated ion channel from the nicotinic acetylcholine receptor family", Nature Letters (2007), 445:116-119.
Boyden et al., "Millisecond-timescale, genetically targeted optical control of neural activity", Nature Neuroscience (2005), 8(9):1263-1268.
Bi et al., "Ectopic Expression of a Microbial-Type Rhodopsin Restores Visual Responses in Mice with Photoreceptor Degeneration", Neuron (2006), 50(1):23-33.
Bi et al., "Synaptic Modifications in Cultured Hippocampal Neurons: Dependence on Spike Timing, Synaptic Strength, and Postsynaptic Cell Type", Journal of Neuroscience (1998), 18(24):10464-10472.
Blomer et al., "Highly Efficient and Sustained Gene Transfer in Adult Neurons with Lentivirus Vector", Journal of Virology (1997), 71(9):6641-6649.
Braun, "Two Light-activated Conductances in the Eye of the Green Alga Volvox carteri", Biophys J. (1999), 76(3):1668-1678.
Brinton et al., "Preclinical analyses of the therapeutic potential of allopregnanolone to promote neurogenesis in vitro and in vivo in transgenic mouse model of Alzheimer's disease", Current Alzheimer Research (2006), 3(1):11-17.
Brosenitsch et al., "Physiological Patterns of Electrical Stimulation Can Induce Neuronal Gene Expression by Activating N-Type Calcium Channels", Journal of Neuroscience (2001), 21(8):2571-2579.
Brown et al., "Long-term potentiation induced by θ frequency stimulation is regulated by a protein phosphate-operated gate", The Journal of Neuroscience (2000), 20(21):7880-7887.
Callaway et al., "Photostimulation using caged glutamate reveals functional circuitry in living brain slices", Proc. Natl. Acad. Sci. USA. (1993), 90:7661-7665.
Campagnola et al., "Fiber-coupled light-emitting diode for localized photostimulation of neurons expressing channelrhodopsin-2", Journal of Neuroscience Methods (2008), 169: Issue 1. Abstract only.
Cardin et al., "Driving Fast spiking Cells Induces Gamma Rhythm and Controls Sensory Responses", Nature (2009), 459(7247):663-667.
Cazillis et al., "VIP and PACAP induce selective neuronal differentiation of mouse embryonic stem cells", Eur J Neurosci (2004), 19(4):798-808.
Cenatiempo, "Prokaryotic gene expression in vitro: transcription-translation coupled systems", Biochimie (1986), 68(4):505-515.
Chow et al., "Optogenetics and translational medicine", Sci Transl Med. (2013), 5(177):177.
Claudio et al., "Nucleotide and deduced amino acid sequences of Torpedo californica acetylcholine receptor gamma subunit", PNAS USA (1983), 80:1111-1115.
Collingridge et al., "Inhibitory post-synaptic currents in rat hippocampal CA1 neurones", J. Physiol. (1984), 356:551-564.
Covington et al., "Antidepressant Effect of Optogenetic Stimulation of the Medial Prefrontal Cortex", Journal of Neuroscience (2010), 30(48):16082-16090.
Crouse et al., "Expression and amplification of engineered mouse dihydrofolate reductase minigenes", Mol. Cell. Biol. (1983), 3(2):257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus", J. Electron. Microsc. Tech. (1990), 15(4):352-368.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology (1991), 310:316-336.
Cui et al., "Electrochemical deposition and characterization of conducting polymer polypyrrole/PSS on multichannel neural probes," Sensors and Actuators (2001), 93(1):8-18.
Date et al., "Grafting of Encapsulated Dopamine-Secreting Cells in Parkinson's Disease: Long-Term Primate Study", Cell Transplant (2000), 9:705-709.
Dalva et al., "Rearrangements of Synaptic Connections in Visual Cortex Revealed by Laser Photostimulation", Science (1994), 265:255-258.
Dederen et al., "Retrograde neuronal tracing with cholera toxin B subunit: comparison of three different visualization methods", Histochemical Journal (1994), 26:856-862.
De Foubert et al., "Fluoxetine-Induced Change in Rat Brain Expression of Brain-Derived Neurotrophic Factor Varies Depending on Length of Treatment," Neuroscience (2004), 128:597-604.
Deisseroth et al., "Signaling from Synapse to Nucleus: Postsynaptic CREB Phosphorylation During Multiple Forms of Hippocampal Synaptic Plasticity", Neuron (1996), 16:89-101.
Deisseroth et al., "Translocation of Calmodulin to the Nucleus Supports CREB Phosphorylation in Hippocampal Neurons", Nature (1998), 392:198-202.
Deisseroth et al., "Signaling from Synapse to Nucleus: the logic Behind the Mechanisms", Currrent Opinion in Neurobiology (2003), 13:354-365.
Deisseroth et al., "Excitation-neurogenesis Coupling in Adult Neural Stem/Progenitor Cells", Neuron (2004), 42:535-552.
Deisseroth, "Next-generation optical technologies for illuminating genetically targeted brain circuits", The Journal of Neuroscience (2006), 26(41):10380-10386.
Deisseroth, et al., "Controlling the Brain with Light", Scientific American (2010), 303:48-55.
Delaney et al., "Evidence for a long-lived 13-cis-containing intermediate in the photocycle of the leu 93 → ala bacteriorhodopsin mutant", J. Physical Chemistry B (1997), 101(29):5619-5621.
Denk et al., "Anatomical and functional imaging of neurons using 2-photon laser scanning microscopy", Journal of Neuroscience Methods (1994), 54:151-162.

(56) References Cited

OTHER PUBLICATIONS

Ditterich et al., "Microstimulation of visual cortex affects the speed of perceptual decisions", Nature Neuroscience (2003), 6(8):891-898.
Dittgen et al., "Lentivirus-based genetic manipulations of cortical neurons and their optical and electrophysiological monitoring in vivo", PNAS (2004), 101(52):18206-18211.
Douglass et al., "Escape Behavior Elicited by Single, Channelrhodopsin-2-evoked Spikes in Zebrafish Somatosensory Neurons", Curr Biol. (2008), 18(15):1133-1137.
Ehrlich et al., "Amygdala inhibitory circuits and the control of fear memory", Neuron (2009), 62:757-771.
Eijkelkamp et al., "Neurological perspectives on voltage-gated sodium channels", Brain (2012), 135:2585-2612.
Emerich et al., "A Novel Approach to Neural Transplantation in Parkinson's Disease: Use of Polymer-Encapsulated Cell Therapy", Neuroscience and Biobehavioral Reviews (1992), 16:437-447.
Ensell et al., "Silicon-based microelectrodes for neurophysiology, micromachined from silicon-on-insulator wafers", Med. Biol. Eng. Comput. (2000), 38:175-179.
Eisen, "Treatment of amyotrophic lateral sclerosis", Drugs Aging (1999), 14(3):173-196.
Ernst et al., "Photoactivation of Channelrhodopsin", J. Biol. Chem. (2008), 283(3):1637-1643.
Evanko, "Optical excitation yin and yang", Nature Methods (2007), 4:384.
Esposito et al., "The integrase family of tyrosine recombinases: evolution of a conserved active site domain", Nucleic Acids Research (1997), 25(18):3605-3614.
Fabian et al., "Transneuronal transport of lectins", Brain Research (1985), 344:41-48.
Falconer et al., "High-throughput screening for ion channel modulators", Journal of Biomolecular Screening (2002), 7(5):460-465.
Farber et al., "Identification of Presynaptic Neurons by Laser Photostimulation", Science (1983), 222:1025-1027.
Feng et al., "Imaging Neuronal Subsets in Transgenic Mice Expressing Multiple Spectral Variants of GFP", Neuron (2000), 28:41-51.
Fenno et al., "The development and application of optogenetics", Annual Review of Neuroscience (2011), 34(1):389-412.
Fiala et al., "Optogenetic approaches in neuroscience", Current Biology (2010), 20(20):R897-R903.
Fisher et al., "Spatiotemporal Activity Patterns During Respiratory Rhythmogenesis in the Rat Ventrolateral Medulla," The Journal of Neurophysiol (2006), 95:1982-1991.
Fitzsimons et al., "Promotors and Regulatory Elements that Improve Adeno-Associated Virus Transgene Expression in the Brain", Methods (2002), 28:227-236.
Foster, "Bright blue times", Nature (2005), 433:698-699.
Fox et al., "A gene neuron expression fingerprint of C. elegans embryonic motor neurons", BMC Genomics (2005), 6(42):1-23.
Garrido et al., "A targeting motif involved in sodium channel clustering at the axonal initial segment", Science (2003), 300(5628):2091-2094.
Genbank Accession No. DQ094781 (Jan. 15, 2008).
Gelvich et al., "Contact flexible microstrip applicators (CFMA) in a range from microwaves up to short waves", IEEE Transactions on Biomedical Engineering (2002), 49(9):1015-1023.
Gigg et al., "Glutamatergic hippocampal formation projections to prefrontal cortex in the rat are regulated by GABAergic inhibition and show convergence with glutamatergic projections from the limbic thalamus", Hippocampus (1994), 4(2):189-198.
Gilman et al., "Isolation of sigma-28-specific promoters from *Bacillus subtilis* DNA" Gene (1984), 32(1-2):11-20.
Glick et al., "Factors affecting the expression of foreign proteins in *Escherichia coli*", Journal of Industrial Microbiology (1987), 1(5):277-282.
Goekoop et al., "Cholinergic challenge in Alzheimer patients and mild cognitive impairment differentially affects hippocampal activation—a pharmacological fMRI study", Brain (2006), 129:141-157.
Gold et al., "Representation of a perceptual decision in developing oculomotor commands", Nature (2000), 404:390-394.
Gonzalez et al., "Cell-Based Assays and Instrumentation for Screening Ion-Channel Targets", DDT (1999), 4(9):431-439.
Gordon et al., "Regulation of Thy-1 Gene Expression in Transgenic Mice", Cell (1987), 50:445-452.
Gorelova et al., "The course of neural projection from the prefrontal cortex to the nucleus accumbens in the rat", Neuroscience (1997), 76(3):689-706.
Goshen et al., "Dynamics of Retrieval Strategies for Remote Memories", Cell (2011), 147:678-589.
Gottesman et al., "Bacterial regulation: global regulatory networks", Ann. Rev. Genet. (1984), 18:415-441.
Gradinaru et al., "Targeting and readout strategies for fast optical neural control in vitro and in vivo", J Neuroscience (2007), 27(52):14231-14238.
Gradinaru et al., "ENpHR: a Natronomonas Halorhodopsin Enhanced for Optogenetic Applications", Brain Cell Biol. (2008), 36(1-4):129-139.
Gradinaru et al., "Optical Deconstruction of Parkinsonian neural circuitry", Science (2009), 324(5925):354-359.
Gradinaru et al., "Molecular and Cellular Approaches for Diversifying and Extending Optogenetics", Cell (2010), 141(1):154-165.
Greenberg et al., "Three-year outcomes in deep brain stimulation for highly resistant obsessive-compulsive disorder", Neuropsychopharmacology (2006), 31:2384-2393.
Gregory et al., "Integration site for *Streptomyces* phage φBT1 and development of site-specific integrating vectors", Journal of Bacteriology (2003), 185(17):5320-5323.
Groth et al., "Phage integrases: biology and applications", Journal of Molecular Biology (2004), 335:667-678.
Groth et al., "A phage integrase directs efficient site-specific integration in human cells", PNAS (2000), 97(11):5995-6000.
Guatteo et al., "Temperature sensitivity of dopaminergic neurons of the substantia nigra pars compacta: Involvement of transient receptor potential channels", Journal of Neurophysiol. (2005), 94:3069-3080.
Gulick et al., "Transfection using DEAE-Dextran" Supplement 40, Current Protocols in Molecular Biology (1997), Supplement 40:9.2.1-9.2.10.
Gunaydin et al., "Ultrafast optogenetic control", Nature Neuroscience (2010), 13(3):387-392.
Gur et al., "A Dissociation Between Brain Activity and Perception: Chromatically Opponent Cortical Neurons Signal Chromatic Flicker that is not Perceived", Vision Research (1997), 37(4):377-382.
Hallet et al., "Transposition and site-specific recombination: adapting DNA cut-and-paste mechanisms to a variety of genetic rearrangements", FEMS Microbiology Reviews (1997), 21(2):157-178.
Hamer et al., "Regulation In Vivo of a cloned mammalian gene: cadmium induces the transcription of a mouse metallothionein gene in SV40 vectors", Journal of Molecular Applied Genetics (1982), 1(4):273-288.
Han et al., "Multiple-Color Optical Activation, Silencing, and Desynchronization of Neural Activity with Single-Spike Temporal Resolution", PLoS One (2007), 2(3):1-12.
Han et al., "Two-color, bi-directional optical voltage control of genetically-targeted neurons", CoSyne (2007), Abstract Presentation, Poster III-67, p. 269, Presented Feb. 24, 2007.
Hausser et al., "Tonic Synaptic Inhibition Modulates Neuronal Output Pattern and Spatiotemporal Synaptic Integration", Neuron (1997), 19:665-678.
Hegemann et al., "All-trans Retinal Constitutes the Functional Chromophore in *Chlamydomonas rhodopsin*", Biophys. J. (1991), 60:1477-1489.
Herlitze et al., "New Optical Tools for Controlling Neuronal Activity", Curr. Opin. Neurobiol. (2007), 17(1):87-94.
Herry et al., "Switching on and off fear by distinct neuronal circuits", Nature (2008), 454:600-606.
Hikida et al., "Increased sensitivity to cocaine by cholingergic cell ablation in nucleus accumbens," PNAS (2001), 98(23):13351-13354.

(56) References Cited

OTHER PUBLICATIONS

Hikida et al., "Acetlycholine enhancement in the nucleus accumbens prevents addictive behaviors of cocaine and morphine", PNAS (2003), 100(10):6169-6173.
Hildebrandt et al., "Bacteriorhodopsin expressed in *Schizosaccharomyces pombe* pumps protons through the plasma membrane", PNAS (1993), 90:3578-3582.
Hira et al., "Transcranial optogenetic stimulation for functional mapping of the motor cortex", J Neurosci Methods (2009), 179:258-263.
Hirase et al., "Multiphoton stimulation of neurons", J Neurobiol (2002), 51(3):237-247.
Hodaie et al., "Chronic Anterior Thalamus Stimulation for Intractable Epilepsy", Epilepsia (2002), 43:603-608.
Hoffman et al., "K+ Channel Regulation of Signal Propagation in Dendrites of Hippocampal Pyramidal Neurons", Nature (1997), 387:869-874.
Hofherr et al., "Selective Golgi export of Kir2.1 controls the stoichiometry of functional Kir2.x channel heteromers", Journal of Cell Science (2005), 118:1935-1943.
Hosokawa et al., "Imaging spatio-temporal patterns of long-term potentiation in mouse hippocampus", Philos. Trans. R. Soc. Lond. B. (2003), 358:689-693.
Hustler et al., "Acetylcholinesterase staining in human auditory and language cortices: regional variation of structural features", Cereb Cortex (1996), 6(2):260-70.
Hynynen et al., "Clinical applications of focused ultrasound—The brain", Int. J. Hyperthermia (2007), 23(2):193-202.
International Search Report for International Application No. PCT/US2009/053474, dated Oct. 8, 2009.
Isenberg et al., "Cloning of a Putative Neuronal Nicotinic Aceylcholine Receptor Subunit", Journal of Neurochemistry (1989), 52:988-991.
Iyer et al., "Virally mediated optogenetic excitation and inhibition of pain in freely moving nontransgenic mice", Nat Biotechnol. (2014), 32(3):274-278.
Ji et al., "Light-evoked Somatosensory Perception of Transgenic Rats that Express Channelrhodopsin-2 in Dorsal Root Ganglion Cells", PLoS One (2012), 7(3):e32699.
Jimenez et al., "Nuclear disconnection within the amygdala reveals a direct pathway to fear", Learning Memory (2009), 16:766-768.
Jekely, "Evolution of Phototaxis", Phil. Trans. R. Soc. B (2009), 364:2795-2808.
Jennings et al., "Distinct extended amygdala circuits for divergent motivational states," Nature (2013), 496:224-228.
Johansen et al., "Optical Activation of Lateral Amygdala Pyramidal Cells Instructs Associative Fear Learning", PNAS (2010), 107(28):12692-12697.
Johnston et al., "Isolation of the yeast regulatory gene GAL4 and analysis of its dosage effects on the galactose/melibiose regulon", PNAS (1982), 79:6971-6975.
Kandel et al., "Electrophysiology of Hippocampal Neurons: I. Sequential Invasion and Synaptic Organization", J Neurophysiol (1961), 24:225-242.
Kandel et al., "Electrophysiology of Hippocampal Neurons: II. After-Potentials and Repetitive Firing", J Neurophysiol. (1961), 24:243-259.
Karreman et al., "On the use of double FLP recognition targets (FRTs) in the LTR of retroviruses for the construction of high producer cell lines", Nucleic Acids Research (1996), 24(9):1616-1624.
Kato et al., "Present and future status of noninvasive selective deep heating using RF in hyperthermia", Med & Biol. Eng. & Comput 31 Supp: S2-11, 1993. Abstract. Page S2 only.
Katz et al., "Scanning laser photostimulation: a new approach for analyzing brain circuits", Journal of Neuroscience Methods (1994), 54:205-218.
Khodakaramian et al., "Expression of Cre Recombinase during Transient Phage Infection Permits Efficient Marker Removal in *Streptomyces*", Nucleic Acids Research (2006), 34(3:e20):1-5.

Khosravani et al., "Voltage-Gated Calcium Channels and Idiopathic Generalized Epilepsies", Physiol. Rev. (2006), 86:941-966.
Kianianmomeni et al., "Channelrhodopsins of Volvox carteri are Photochromic Proteins that are Specifically Expressed in Somatic Cells under Control of Light, Temperature, and the Sex Inducer", Plant Physiology (2009), 151(1):347-366.
Kim et al., "PDZ domain proteins of synapses", Nature Reviews Neuroscience (2004), 5(10):771-781.
Kim et al., "Diverging neural pathways assemble a behavioural state from separable features in anxiety", Nature (2013), 496(7444):219-223.
Kim et al., "Light-Driven Activation of $\beta$2-Adrenergic Receptor Signaling by a Chimeric Rhodopsin Containing the $\beta$2-Adrenergic Receptor Cytoplasmic Loops," Biochemistry (2005), 44(7):2284-2292.
Kingston et al., "Transfection of DNA into Eukaryotic Cells," Supplement 63, Current Protocols in Molecular Biology, 1996, 9.1.1-9.1.11, 11 pages.
Kingston et al., "Transfection and Expression of Cloned DNA," Supplement 31, Current Protocols in Immunology, 1999, 10.13.1-10.13.9.
Kinoshita, et al., "Optogenetically Induced Supression of Neural Activity in the Macaque Motor Cortex", Poster Sessions Somatomotor System, Others, Society for Neuroscience Meeting (2010), pp. 141-154.
Kita et al., "Effects of dopamine agonists and antagonists on optical responses evoked in rat frontal cortex slices after stimulation of the subcortical white matter," Exp. Brain Research (1999), 125:383-388.
Kitabatake et al., "Impairment of reward-related learning by cholinergic cell ablation in the striatum", PNAS (2003), 100(13):7965-7970.
Kitayama et al., "Regulation of neuronal differentiation by N-methyl-D-aspartate receptors expressed in neural progenitor cells isolated from adult mouse hippocampus," Journal of Neurosci Research (2004), 76(5):599-612.
Klausberger et al., "Brain-state- and cell-type-specific firing of hippocampal interneurons in vivo", Nature (2003), 421:844-848.
Kocsis et al., "Regenerating Mammalian Nerve Fibres: Changes in Action Potential Wave from and Firing Characteristics Following Blockage of Potassium Conductance", Proc. R. Soc. Lond. (1982), B 217:77-87.
Kokel et al., "Photochemical activation of TRPA1 channels in neurons and animals", Nat. Chem. Biol. (2013), 9(4):257-263.
Knopfel et al., "Optical Probing of Neuronal Circuit Dynamics: Genetically Encoded Versus Classical Fluorescent Sensors", Trends Neurosci (2006), 29(3):160-166.
Kuhlman et al., "High-Resolution Labeling and Functional Manipulation of Specific Neuron Types in Mouse Brain by Cre-Activated Viral Gene Expression" PLoS One (2008), e2005, 3(4):1-11.
Kunkler et al., "Optical Current Source Density Analysis in Hippocampal Organotypic Culture Shows that Spreading Depression Occurs with Uniquely Reversing Current," The Journal of Neuroscience (2005), 25(15):3952-3961.
Lalumiere, "A new technique for controlling the brain: optogenetics and its potential for use in research and the clinic", Brain Stimulation (2011), 4:1-6.
Lammel et al., "Input-specific control of reward and aversion in the ventral tegmental area", Nature, 2012, 491(7423): 212-217.
Lanyi et al., "The primary structure of a Halorhodopsin from Natronobacterium Pharaonis" Journal of Biological Chemistry (1990), 265(3):1253-1260.
Landy, "Mechanistic and structural complexity in the site-specific recombination pathways of Int and FLP", Current Opinion in Genetics and Development (1993), 3:699-707.
Lee et al., "Sterotactic Injection of Adenoviral Vectors that Target Gene Expression to Specific Pituitary Cell Types: Implications for Gene Therapy", Neurosurgery (2000), 46(6):1461-1469.
Lee et al., "Potassium Channel Gene Therapy Can Prevent Neuron Death Resulting from Necrotic and Apoptotic Insults", Journal of Neurochemistry (2003), 85:1079-1088.
Levitan et al., "Surface Expression of Kv1 Voltage-Gated K+ Channels is Governed by a C-terminal Motif," Trends Cardiovasc. Med. (2000), 10(7):317-320.

(56) References Cited

OTHER PUBLICATIONS

Li et al., "Surface Expression of Kv1 Channels is Governed by a C-Terminal Motif", J. Bio. Chem. (2000), 275(16):11597-11602.
Li et al., "Fast noninvasive activation and inhibition of neural and network activity by vertebrate rhodopsin and green algae channel rhodopsin." PNAS (2005), 102(49):17816-17821.
Lim et al., "A Novel Targeting Signal for Proximal Clustering of the Kv2.1K+ Channel in Hippocampal Neurons", Neuron (2000), 25:385-397.
Lima, et al., "Remote Control of Behavior through Genetically Targeted Photostimulation of Neurons", Cell (2005), 121:141-152.
Liman et al., "Subunit Stoichiometry of a Mammalian K+ Channel Determined by Construction of Multimedia cans," Neuron (1992), 9:861-871.
Liu et al., "Optogenetics 3.0", Cell (2010), 141(1):22-24.
Lin, "A user's guide to channel rhodopsin variants: features, limitations and future developments", Exp. Physiol. (2010), 96(1):19-25.
Liske et al., "Optical inhibition of motor nerve and muscle activity in vivo", Muscle Nerve (2013), 47(6):916-921.
Llewellyn et al., "Orderly recruitment of motor units under optical control in vivo", Nat Med. (2010), 16(10):1161-1165.
Louis et al., "Cloning and sequencing of the cellular-viral junctions from the human adenovirus type 5 transformed 293 cell line," Virology (1997), 233:423-429.
Loetterle et al., "Cerebellar Stimulation: Pacing the Brain", American Journal of Nursing (1975), 75(6):958-960.
Lonnerberg et al., "Regulatory Region in Choline Acetyltransferase Gene Directs Developmental and Tissue-Specific Expression in Transgenic mice", Proc. Natl. Acad. Sci. USA (1995), 92(9):4046-4050.
Luecke et al., "Structural Changes in Bacteriorhodopsin During Ion Transport at 2 Angstrom Resolution," Science (1999), 286:255-260.
Lyznik et al., "FLP-mediated recombination of FRT sites in the maize genome," Nucleic Acids Research (1996), 24(19):3784-3789.
Ma et al., "Role of ER Export Signals in Controlling Surface Potassium Channel Numbers," Science (2001), 291:316-319.
Malin et al., "Involvement of the rostral anterior cingulate cortex in consolidation of inhibitory avoidance memory: Interaction with the basolateral amygdala", Neurobiol Learn Mem. (2007), 87(2):295-302.
Marin et al., The Amino Terminus of the Fourth Cytoplasmic Loop of Rhodopsin Modulates Rhodopsin-Transduction Interaction, The Journal of Biological Chemistry (2000), 275:1930-1936.
Mancuso et al., "Optogenetic probing of functional brain circuitry", Experimental Physiology (2010), 96(1):26-33.
Mann et at., "Perisomatic Feedback Inhibition Underlies Cholinergically Induced Fast Network Oscillations in the Rat Hippocampus in Vitro," Neuron (2005), 45:105-117.
Mattis et al., "Principles for applying optogenetic tools derived from direct comparative analysis of microbial opsins", Nat Methods (2011), 9(2):159-72.
Mattson, "Apoptosis in Neurodegenerative Disorders", Nature Reviews (2000), 1:120-129.
Mayberg et al., "Deep Brain Stimulation for Treatment-Resistant Depression," Focus (2008), 6(1):143-154.
Mayford et al., "Control of memory formation through regulated expression of CaMKII transgene", Science (1996), 274(5293):1678-1683.
McAllister, "Cellular and Molecular Mechanisms of Dendrite Growth", Cereb Cortex (2000), 10(10):963-973.
McKnight, "Functional relationships between transcriptional control signals of the thymidine kinase gene of herpes simplex virus", Cell (1982), 31:355-365.
Melyan et al., "Addition of human melanopsin renders mammalian cells Photoresponsive", Nature (2005), 433:741-745.
Mermelstein et al., "Critical Dependence of cAMP Response Element-Binding Protein Phosphorylation on L-Type Calcium Channels Supports a Selective Response to EPSPs in Preference to Action Potentials", The Journal of Neuroscience (2000), 20(1):266-273.

Meyer et al., "High density interconnects and flexible hybrid assemblies for active biomedical implants," IEEE Transactions on Advanced Packaging (2001), 24(3):366-372.
Milella et al., "Opposite roles of dopamine and orexin in quinpirole-induced excessive drinking: a rat model of psychotic polydipsia", Psychopharmacology (2010), 211:355-366.
Monje et al., "Irradiation Induces Neural Precursor-Cell Dysfunction", Natural Medicine (2002), 8(9):955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology (1999), 80:571-583.
Mortensen et al., "Selection of Transfected Mammalian Cells," Supplement 86, Current Protocols in Molecular Biology (1997), 9.5.1-09.5.19.
Mourot et al., "Rapid Optical Control of Nociception with an Ion Channel Photoswitch", Nat Methods (2012), 9(4):396-402.
Nacher, et al., "NMDA receptor antagonist treatment increases the production of new neurons in the aged rat hippocampus", Neurobiology of Aging (2003), 24(2):273-84.
Nagel et al., "Functional Expression of Bacteriorhodopsin in Oocytes Allows Direct Measurement of Voltage Dependence of Light Induced H+ Pumping," FEBS Letters (1995), 377:263-266.
Nagel et al., "Channelrhodopsin-I: a light-gated proton channel in green algae", Science (2002), 296:2395-2398.
Nagel et al., "Channelrhodopsin-2, a directly light-gated cation-selective membrane channel", PNAS (2003), 100(24):13940-13945.
Nakagami et al., "Optical Recording of Trisynaptic Pathway in Rat Hippocampal Slices with a Voltage-Sensitive Dye", Neuroscience (1997), 81(1):1-8.
Naqvi et al., "Damage to the insula disrupts addiction to cigarette smoking," Science (2007), 315:531-534.
Natochin et al., "Probing rhodopsin-transducin interaction using *Drosophila* Rh1-bovine rhodopsin chimeras," Vision Res. (2006), 46(27):4575-81.
Nieh et al., "Optogenetic dissection of neural circuits underlying emotional valence and motivated behaviors", Brain Research (E-pub 2012), 1511:73-92.
Nirenberg et al., "The Light Response of Retinal Ganglion Cells is Truncated by a Displaced Amacrine Circuit", Neuron (1997), 18:637-650.
Nonet, "Visualization of synaptic specializations in live C. elegans with synaptic vesicle protein-GFP fusions", J. Neurosci. Methods (1999), 89:33-40.
Nunes-Duby et al., "Similarities and differences among 105 members of the Int family of site-specific recombinases", Nucleic Acids Research (1998), 26(2):391-406.
O'Gorman et al., "Recombinase-mediated gene activation and site-specific integration in mammalian cells", Science (1991), 251(4999):1351-1355.
Olivares, "Phage R4 integrase mediates site-specific integration in human cells", Gene (2001), 278:167-176.
Ory et al., "A stable human-derived packaging cell line for production of high titer retrovirus/vesicular stomatitis virus G pseudotypes," PNAS (1996), 93:11400-11406.
Palmer et al., "The Adult Rat Hippocampus Contains Primordial Neural Stem Cells", Molecular and Cellular Neuroscience (1997), 8:389-404.
Palmer et al., "Fibroblast Growth Factor-2 Activates a Latent Neurogenic Program in Neural Stem Cells from Diverse Regions of the Adult CNS", The Journal of Neuroscience (1999), 19:8487-8497.
Pan et al., "Functional Expression of a Directly Light-Gated Membrane Channel in Mammalian Retinal Neurons: A Potential Strategy for Restoring Light Sensitivity to the Retina After Photoreceptor Degeneration," Investigative Ophthalmology & Visual Science (2005), 46 E-Abstract 4631. Abstract only.
Panda et al., "Illumination of the Melanopsin Signaling Pathway", Science (2005), 307:600-604.

(56) References Cited

OTHER PUBLICATIONS

Pape et al., "Plastic Synaptic Networks of the Amygdala for the Acquisition, Expression, and Extinction of Conditioned Fear", Physiol. Rev. (2010), 90:419-463.
Paulhe et al., "Specific Endoplasmic Reticulum Export Signal Drives Transport of Stem Cell Factor (Kitl) to the Cell Surface," The Journal of Biological Chemistry (2004), 279(53):55545-55555.
Pear, "Transient Transfection Methods for Preparation of High-Titer Retroviral Supernatants" Supplement 68, Current Protocols in Molecular Biology (1996), 9.11.1-9.11.18.
Peralvarez-Marin et al., "Inter-helical hydrogen bonds are essential elements for intra-protein signal transduction: The role of Asp115 in bacteriorhodopsin transport function", J. Mol. Biol. (2007), 368:666-676.
Peterlin et al., "Optical probing of neuronal circuits with calcium indicators," PNAS (2000), 97(7):3619-3624.
Petersen et al., "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience (2003), 23(3):1298-1309.
Petrecca et al., "Localization and Enhanced Current Density of the Kv4.2 Potassium Channel by Interaction with the Actin-Binding Protein Filamin," The Journal of Neuroscience (2000), 20(23):8736-8744.
Pettit et al., "Local Excitatory Circuits in the Intermediate Gray Layer of the Superior Colliculus", J Neurophysiol. (1999), 81(3):1424-1427.
Pinkham et al., "Neural bases for impaired social cognition in schizophrenia and autism spectrum disorders", Schizophrenia Research (2008), 99:164-175.
Potter, "Transfection by Electroporation." Supplement 62, Current Protocols in Molecular Biology (1996), 9.3.1-9.3.6.
Pouille et al., "Routing of spike series by dynamic circuits in the hippocampus", Nature (2004), 429:717-723.
Qiu et al., "Induction of photosensitivity by heterologous expression of melanopsin", Nature (2005), 433:745-749.
Rammes et al., "Synaptic Plasticity in the Basolateral Amygdala in Transgenic Mice Expressing Dominant-Negative cAMP Response Element-binding Protein (CREB) in Forebrain", Eur J. Neurosci (2000), 12(7):2534-46.
Randic et al., "Long-term Potentiation and Long-term Depression of Primary Afferent Neurotransmission in the Rat Spinal Cord", Journal of Neuroscience, (1993), 13(12):5228-41.
Rathnasingham et al., "Characterization of implantable microfabricated fluid delivery devices," IEEE Transactions on Biomedical Engineering (2004), 51(1):138-145.
Rein et al., "The Optogenetic (r)evolution", Mol. Genet. Genomics (2012), 287(2):95-109.
Remy et al., "Depression in Parkinson's Disease: Loss of Dopamine and Noradrenaline Innervation in the Limbic System", Brain (2005), 128(6):1314-1322.
Ritter et al., "Monitoring Light-induced Structural Changes of Channelrhodopsin-2 by UV-Visible and Fourier Transform Infrared Spectroscopy", The Journal of Biological Chemistry (2008), 283(50):35033-35041.
Rivera et al., "BDNF-Induced TrkB Activation Down-Regulates the K+-Cl-Cotransporter KCC2 and Impairs Neuronal Cl-Extrusion", The Journal of Cell Biology (2002), 159:747-752.
Rosenkranz et al., "The prefrontal cortex regulates lateral amygdala neuronal plasticity and responses to previously conditioned stimuli", J. Neurosci. (2003), 23(35):11054-11064.
Rousche et al., "Flexible polyimide-based intracortical electrode arrays with bioactive capability," IEEE Transactions on Biomedical Engineering (2001), 48(3):361-371.
Rubinson et at., "A lentivirus-based system to functionally silence genes in primary mammalian cells, stem cells and transgenic mice by RNA interference," Nature Genetics (2003), 33:401-406.
Rudiger et at., "Specific arginine and threonine residues control anion binding and transport in the light-driven chloride pump halorhodopsin," The EMBO Journal (1997), 16(13):3813-3821.
Salzman et al., "Cortical microstimulation influences perceptual judgements of motion direction", Nature (1990), 346:174-177.
Sajdyk et al., "Excitatory Amino Acid Receptors in the Basolateral Amygdala Regulate Anxiety Responses in the Social Interaction Test", Brain Research (1997), 764:262-264.
Sato et al., "Role of Anion-binding Sites in cytoplasmic and extracellular channels of *Natronomonas pharaonis* halorhodopsin," Biochemistry (2005), 44:4775-4784.
Sauer, "Site-specific recombination: developments and applications," Current Opinion in Biotechnology (1994), 5(5):521-527.
Schiff et al., "Behavioral improvements with thalamic stimulation after severe traumatic brain injury," Nature (2007), 448:600-604.
Schlaepfer et al., "Deep Brain stimulation to Reward Circuitry Alleviates Anhedonia in Refractory Major Depression," Neuropsychopharmacology (2008), 33:368-377.
Schroll et al., "Light-induced activation of distinct modulatory neurons triggers appetitive or aversive learning in *Drosophila larvae*", Current Biology (2006), 16(17):1741-1747.
Sclimenti et al., "Directed evolution of a recombinase for improved genomic integration at a native human sequence," Nucleic Acids Research (2001), 29(24):5044-5051.
Shepherd et al., "Circuit Analysis of Experience-Dependent Plasticity in the Developing Rat Barrel Cortex", Neuron (2003), 38:277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Silver et al., "Amino terminus of the yeast GAL4 gene product is sufficient for nuclear localization" PNAS (1984), 81(19):5951-5955.
Simmons et al., "Localization and function of NK3 subtype Tachykinin receptors of layer pyramidal neurons of the guinea-pig medial prefrontal cortex", Neuroscience (2008), 156(4):987-994.
Sineshchekov et al., "Two Rhodopsins Mediate Phototaxis to Low and High Intensity Light in Chlamydomas Reinhardtil", PNAS (2002), 99(13):8689-94.
Singer et al., "Elevated Intrasynaptic Dopamine Release in Tourette's Syndrome Measured by PET," American Journal of Psychiatry (2002), 159:1329-1336.
Slamovits et al., "A bacterial proteorhodopsin proton pump in marie eukaryotes", Nature Comm (2011), 2:183.
Slimko et al., "Selective Electrical Silencing of Mammalian Neurons In Vitro by the use of Invertebrate Ligand-Gated Chloride Channels", The Journal of Neuroscience (2002), 22(17):7373-7379.
Smith et al., "Diversity in the serine recombinases", Molecular Microbiology (2002) 44(2):299-307.
Sohal et al., "Parvalbumin neurons and gamma rhythms enhance cortical circuit performance", Nature (2009), 459(7247):698-702.
Song et al., "Differential Effect of TEA on Long-Term Synaptic Modification in Hippocampal CA1 and Dentate Gyrus in vitro." Neurobiology of Learning and Memory (2001), 76(3):375-387.
Song, "Genes responsible for native depolarization-activated K+ currents in neurons," Neuroscience Research (2002), 42:7-14.
Stark et al., "Catalysis by site-specific recombinases," Trends Genet. (1992), 8(12):432-439.
Stockklausner et al., "A sequence motif responsible for ER export and surface expression of Kir2.0 inward rectifier K+ channels," FEBS Letters (2001), 493:129-133.
Stoll et al., "Phage TP901-I site-specific integrase functions in human cells," Journal of Bacteriology (2002), 184(13):3657-3663.
Swanson, "Lights, Opsins, Action! Optogenetics Brings Complex Neuronal Circuits into Sharper Focus", The Dana Foundation (2009), [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
The Nervous System in Action, Synapses, Chapter 13, http://michaeldmann.net/mann13.html, downloaded Apr. 2014.

(56) References Cited

OTHER PUBLICATIONS

Tamai, "Progress in Pathogenesis and Therapeutic Research in Retinitis Pigmentosa and Age Related Macular Degeneration", Nippon Ganka Gakkai Zasshi (2004), 108(12):750-769.
Tam et al., "Identification of an Outer Segment Targeting Signal in the COOH Terminus of Rhodopsin Using Transgenic *Xenopus laevis*", The Journal of Cell Biology (2000), 151(7):1369-1380.
Takahashi et al., "Diversion of the Sign of Phototaxis in a *Chlamydomonas reinhardtii* Mutant Incorporated with Retinal and Its Analogs," FEBS Letters (1992), 314(3):275-279.
Takahashi et al., "Induction of Pluripotent Stem Cells from Mouse Embryonic and Adult Fibroblast Cultures by Defined Factors", Cell (2006), 126:663-676.
Tatarkiewicz et al., "Reversal of Hyperglycemia in Mice After Subcutaneous Transplantation of Macroencapsulated Islets", Transplantation (1999), 67(5):665-671.
Tønnese et al., "Optogenetic Control of Epileptiform Activity", PNAS (2009), 106(29):12162-7.
Tottene et al., "Familial Hemiplegic Migraine Mutations Increase $Ca^{2+}$ Influx Through Single Human $Ca_v2.1$ Current Density in Neurons", PNAS USA (2002), 99(20):13284-13289.
Towne et al., "Efficient transduction of non-human primate motor neurons after intramuscular delivery of recombinant AAV serotype 6", Gene Ther. (2010), 17(1):141-6.
Towne et al., "Optogenetic control of targeted peripheral axons in freely moving animals", PLoS One (2013), 8(8):e72691.
Towne et al., "Recombinant adeno-associated virus serotype 6 (rAAV2/6)-mediated gene transfer to nociceptive neurons through different routes of delivery", Mol. Pain (2009), 5:52.
Tsau et al., "Distributed Aspects of the Response to Siphon Touch in Aplysia: Spread of Stimulus Information and Cross-Correlation Analysis," The Journal of Neuroscience (1994), 14(7):4167-4184.
Tsai et al., "Phasic Firing in Dopaminergic Neurons in Sufficient for Behavioral Conditioning", Science (2009), 324:1080-1084.
[No Authors Listed], "Two bright new faces in gene therapy," Nature Biotechnology (1996), vol. 14:556.
Tye et. al., "Amygdala circuitry mediating reversible and bidirectional control of anxiety", Nature (2011), 471(7338): pp. 358-362.
Tye et al., "Optogenetic investigation of neural circuits underlying brain disease in animal models," Nature Reviews Neuroscience (2012), 13(4):251-266.
Tye et al., Supplementary Materials: "Amygdala circuitry mediating reversible and bidirectional control of anxiety", Nature (2011), 471(7338):358-362.
"SubName: Full=Channelrhodopsin-1", retrieved from EBI accession No. UNIPROT: B4Y103. Database accession No. B4Y103. Sep. 23, 2008.
Ulmanen et al., "Transcription and translation of foreign genes in *Bacillus subtilis* by the aid of a secretion vector," Journal of Bacteriology (1985), 162(1):176-182.
Van Der Linden, "Functional brain imaging and pharmacotherapy in social phobia: single photon emission computed tomography before and after Treatment with the selective serotonin reuptake inhibitor citalopram," Prog. Neuro-psychopharmacol Biol. Psychiatry (2000), 24(3):419-38.
Vanin, et al., "Development of high-titer retroviral producer cell lines by using Cre-mediated recombination," Journal of Virology (1997), 71(10):7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Vetter et al., "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. (2007), 9:19.1-19.39.
Ward et al., "Construction and characterisation of a series of multi-copy promoter-probe plasmid vectors for *Streptomyces* using the aminoglycoside phosphotransferase gene from Tn5 as indicator", Mol. Gen. Genet. (1986), 203:468-478.
Watson et al., "Targeted transduction patterns in the mouse brain by lentivirus vectors pseudotyped with VSV, Ebola, Mokola, LCMV, or MuLV envelope proteins," Molecular Therapy (2002), 5(5):528-537.
Wang et al., "Direct-current Nanogenerator Driven By Ultrasonic Waves," Science (2007), 316:102-105.
Wang et al., "Molecular Determinants Differentiating Photocurrent Properties of Two Channelrhodopsins from Chlamydomonas", The Journal of Biological Chemistry (2009), 284(9):5685-5696.
Wang et. al., "High-speed mapping of synaptic connectivity using photostimulation in Channelrhodopsin-2 transgenic mice", PNAS (2007) 104(19):8143-8148.
Wang et al., "Mrgprd-Expressing Polymodal Nociceptive Neurons Innervate Most Known Classes of Substantia Gelatinosa Neurons", J Neurosci (2009), 29(42):13202-13209.
Weick et al., "Interactions with PDZ Proteins Are Required for L-Type Calcium Channels to Activate cAMP Response Element-Binding Protein-Dependent Gene Expression," The Journal of Neuroscience (2003), 23(8):3446-3456.
Wells et al., "Application of Infrared light for in vivo neural stimulation," Journal of Biomedical Optics (2005), 10(6):064003-1-064003-12.
Williams et al., "From optogenetic technologies to neuromodulation therapies", Sci Transl Med. (2013), 5(177):177.
Witten et. al., Supporting Online Material for: "Cholinergic Interneurons Control Local Circuit Activity and Cocaine Conditioning", Science (2010), 330:17 pages.
Witten et. al., "Cholinergic Interneurons Control Local Circuit Activity and Cocaine Conditioning", Science (2010), 330(6011):1677-1681.
Xiong et al., "Interregional connectivity to primary motor cortex revealed using MRI resting state images", Hum Brain Mapp. (1999), 8(2-3):151-156.
Yamazoe et al., "Efficient generation of dopaminergic neurons from mouse embryonic stem cells enclosed in hollow fibers", Biomaterials (2006), 27:4871-4880.
Yan et al., "Cloning and Characterization of a Human $\beta,\beta$-Carotene-15, 15'-Dioxygenase that is Highly Expressed in the Retinal Pigment Epithelium", Genomics (2001), 72:193-202.
Yizhar et al., "Optogenetics in neural systems", Neuron Primer (2011), 71(1):9-34.
Yizhar et. al., "Neocortical excitation/inhibition balance in information processing and social dysfunction", Nature (2011), 477:171-178, and Supplemental Materials; 41 pages.
Yoon et al., "A micromachined silicon depth probe for multichannel neural recording," IEEE Transactions Biomedical Engineering (2000), 47(8):1082-1087.
Yoshimura et al., "Excitatory cortical neurons form fine-scale functional networks", Nature (2005), 433:868-873.
Zacharias et al., "Recent advances in technology for measuring and manipulating cell signals," Current Opinion in Neurobiology (2000), 10:416-421.
Zemelman, et al. "Selective Photostimulation of Genetically ChARGed Neurons", Neuron (2002), 33:15-22.
Zemelman et al., "Photochemical gating of heterologous ion channels: Remote control over genetically designated populations of neurons", PNAS (2003), 100(3):1352-1357.
Zhang et al., "Channelrhodopsin-2 and optical control of excitable cells," Nature Methods (2006), 3(10):785-792.
Zhang et al., "Red-Shifted Optogenetic Excitation: a Tool for Fast Neural Control Derived from *Volvox carteri*", Nature Neurosciences (2008), 11(6):631-633.
Zhang, "Multimodal fast optical interrogation of neural circuitry," Nature (2007), 446:633-641.
Zhang et al., "The Microbial Opsin Family of Optogenetic Tools", Cell (2011), 147(7):1146-1457.
Zhao et al., "Improved Expression of Halorhodopsin for Light-Induced Silencing of Neuronal Activity", Brain Cell Biology (2008), 36 (1-4):141-154.
Zrenner, "Will Retinal Implants Restore Vision?" Science (2002), 295(5557):1022-1025.

(56) References Cited

OTHER PUBLICATIONS

Zufferey et al., "Self-Inactivating Lentivirus Vector for Safe and Efficient In Vivo Gene Delivery", Journal of Virology (1998), 72(12):9873-9880.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
U.S. Appl. No. 14/301,718, filed Jun. 11, 2006, Deisseroth et al.
U.S. Appl. No. 14/365,477, filed Jun. 13, 2014, Deisseroth et al.
U.S. Appl. No. 14/385,331, filed Sep. 15, 2014, Deisseroth et al.
U.S. Appl. No. 14/537,290, filed Nov. 10, 2014, Deisseroth et al.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Jones, et al.; "Animal Models of Schizophrenia"; British Journal of Pharmacology; vol. 164, pp. 1162-1194 (2011).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Coleman, et al.; "Assessing Anxiety in Nonhuman Primates"; Ilar Journal; vol. 55, No. 2, pp. 333-346 (2014).
Maestripieri, et al.; "A modest proposal: displacement activities as an indicator of emotions in primates"; Anim. Behav.; vol. 44, pp. 967-979 (1992).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Definition of integral. Merriam-Webster Dictionary, retrieved on Mar. 20, 2017; Retrieved from the internet: <http://www.merriam-webster.com/dictionary/integral>.
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.

(56) References Cited

OTHER PUBLICATIONS

Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Tsuchida; "Nervous Control of Micturition"; The Japanese Journal of Urology; vol. 80, No. 9, pp. 1257-1277 (1989).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "$\beta$2-Adrenergic Receptor Regulation of the Cardiac L-Type $Ca^{2+}$ Channel Coexpressed in a Fibroblast Cell Line"; Receptor; vol. 5, pp. 219-231 (1996).
Smith, et al.; "Proton binding sites involved in the activation of acid-sensing ion channel ASIC2a"; Neuroscience Letters; vol. 426, pp. 12-17 (2007).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Duvarci, et al., "The bed Nucleus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, pp. 46-49.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).
Belzung et al., "Optogenetics to study the circuits of fear-and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011, 15(12): 592-600.
Erbguth et al. "Bimodal Activation of Different Neuron Classes with Spectrally Red-Shifted Channelrhodopsin Chimera C1V1 in Caenorhabditis elegans," PLOS One, 2012, vol. 7 No. 10, pp. e46827/1-9.
Li et al.; "Role of a Helix B Lysine Residue in the Photoactive Site in Channelrhodopsins," Biophysical Journal, 2014, vol. 106, pp. 1607-1617.
Prigge et al.: "Functional Studies of Volvox Channelrhodopsin Chimeras," Biophysical Journal, 2010, vol. 98, No. 3, Suppl. 1, 3694 Poster, 1 page.
Prigge et al.; Color-tuned Channelrhodopsins for Multiwavelength Optogenetics, J. Biol. Chem. 2012, vol. 287, No. 38, pp. 31804-31812.
Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.
Nargeot et al.; Molecular basis of the diversity of calcium channels in cardiovascular tissues Heart Journal, 1997, Supplemental A, A15-A26.

\* cited by examiner

SYSTEM FOR OPTICAL STIMULATION OF TARGET CELLS

RELATED PATENT DOCUMENTS

This application is a continuation of U.S. patent application Ser. No. 11/651,422, filed Jan. 9, 2007, now U.S. Pat. No. 8,926,959, which is a continuation-in-part of U.S. patent application Ser. No. 11/459,636, filed Jul. 24, 2006, now U.S. Pat. No. 8,906,360, which claims the benefit of U.S. Provisional Patent Application No. 60/701,799, filed Jul. 22, 2005, which applications are incorporated herein by reference in their entirety.

FIELD OF THE INVENTION

The present invention relates generally to systems and approaches for stimulating target cells, and more particularly to using an optical device to stimulate the target cells.

BACKGROUND

The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the CNS, and makes neuromodulation a difficult therapeutic endeavor. This architecture of the brain is poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neuron using electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread of electrical current may increase the unintended stimulation of additional cells.

Another method of stimulus uses photosensitive bio-molecular structures to stimulate target cells in response to light. For instance, light activated proteins can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Recently discovered techniques allow for stimulation of cells resulting in the rapid depolarization of cells (e.g., in the millisecond range). Such techniques can be used to control the depolarization of cells such as neurons. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions. For further details on specific implementations of photosensitive bio-molecular structures and methods, reference can be made to "Millisecond-Timescale, Genetically Optical Control of Neural Activity", by Boyden, Edward S. et al., *Nature Neuroscience* 8, 1263-1268 (2005). This reference discusses use of blue-light-activated ion channel channelrhodopsin-2 (ChR2) to cause calcium (Ca++)-mediated neural depolarization, and is fully incorporated herein be reference. Other applicable light-activated ion channels include halorhodopsin (NpHR), in which amber light affects chloride (Cl−) ion flow so as to hyperpolarize neuronal membrane, and make it resistant to firing.

While these and other methods are promising scientific discoveries, there is need for innovations that allow for practical application of these basic mechanisms, such as in vivo neuromodulation, for example, to treat diseases in humans. Often, the specific location at which the photosensitive bio-molecular structure is applied to is critical. Moreover, the process by which light is made able to reach the photosensitive bio-molecular structures can involves obstacles, on the practical level. In many applications, minimal invasiveness of the procedure is paramount. For instance, the brain is a delicate organ and less disruption is usually a paramount issue for surgeries and similar procedures on the brain. Thus, it is sometimes desirable that the extent of any surgical procedure be kept to a minimum. This can be difficult, however, where large devices are needed for the administration of treatment. In some applications the comfort of the patient is also important. Thus, external apparatus can be less than ideal.

These and other issues have presented challenges to the implementation of the stimulus of target cells, including those involving photosensitive bio-molecular structures and those used in similar applications.

SUMMARY

The claimed invention is directed to photosensitive bio-molecular structures and related methods. The present invention is exemplified in a number of implementations and applications, some of which are summarized below.

According to one example embodiment of the present invention, an implantable arrangement is implemented having a light-generation device for generating light. The arrangement also has a biological portion that modifies target cells for stimulation in response to light generated by the light-generation means in vivo.

According to another example embodiment of the present invention, target cells are stimulated using an implantable arrangement. The arrangement includes an electrical light-generation means for generating light and a biological portion. The biological portion has a photosensitive bio-molecular arrangement that responds to the generated light by stimulating target cells in vivo. Stimulation may be manifest as either upregulation, or down-regulation of activity at the target.

According to another example embodiment of the present invention, an implantable device delivers gene transfer vector, such as a virus, which induces expression of photosensitive bio-molecular membrane proteins. The device has a light generator, responsive to (for example, charged by or triggered by) an external signal, to generate light and a biological arrangement that includes the photosensitive biomolecular protein that responds to the generated light by interacting with target cells in vivo. In this manner, the electronic portions of the device may be used to optically stimulate target cells. Stimulation may be manifest as either upregulation (e.g. increased neuronal firing activity), or downregulation (e.g. neuronal hyperpolarization, or alternatively, chronic depolarization) of activity at the target.

According to another example embodiment of the present invention, a method is implemented for stimulating target cells using photosensitive proteins that bind with the target cells. The method includes a step of implanting the photosensitive proteins and a light generating device near the target cells. The light generating device is activated and the photosensitive protein stimulates the target cells in response to the generated light.

Applications include those associated with any population of electrically-excitable cells, including neurons, skeletal, cardiac, and smooth muscle cells, and insulin-secreting pancreatic beta cells. Major diseases with altered excitation-effector coupling include heart failure, muscular dystrophies, diabetes, pain, cerebral palsy, paralysis, depression, and schizophrenia. Accordingly, the present invention has utility in the treatment of a wide spectrum of medical conditions, from Parkinson's disease and brain injuries to cardiac dysrhthmias, to diabetes, and muscle spasm.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
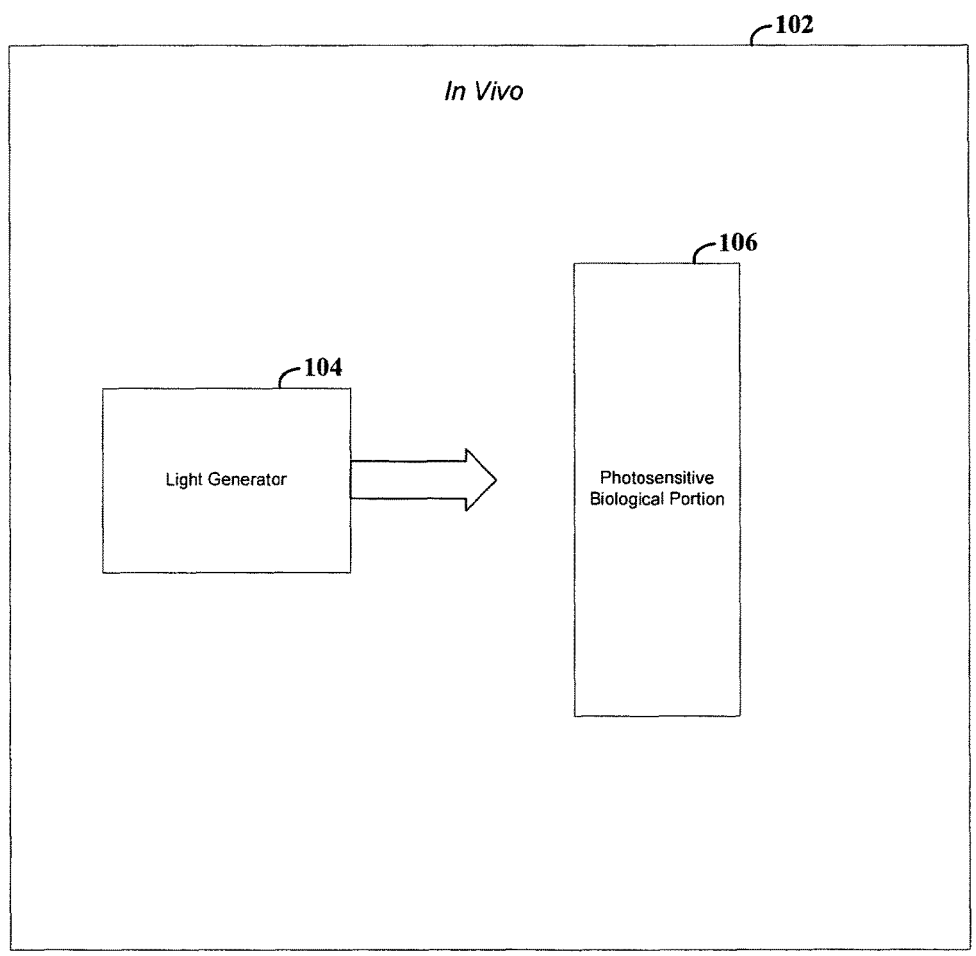
FIG. 1 shows a block diagram of a system for stimulating target cells, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of photosensitive biomolecular structures, and the invention has been found to be particularly suited for use in arrangements and methods dealing with neuron stimulation. While the present invention is not necessarily limited to such applications, various aspects of the invention may be appreciated through a discussion of various examples using this context.

Consistent with one example embodiment of the present invention, target cells are stimulated using an implantable arrangement. The implantable arrangement includes a biological portion that facilitates the stimulation of the target cells in response to receipt of light. The implantable arrangement also includes a light generator for creating light to trigger the stimulus of the target cells.

Consistent with another example embodiment of the present invention, a method is implemented for stimulating target cells in vivo using gene transfer vectors (for example, viruses) capable of inducing photosensitive ion channel growth (for example, ChR2 ion channels). The vectors are implanted in the body, along with the electronic components of the apparatus. A light producing device is implanted near the target cells. The target cells are stimulated in response to light generated by the light producing device.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses by the neuron.

Consistent with another example embodiment of the present invention, the target cells are neurons located in the brain of a mammal. The target cells are genetically modified to express photosensitive bio-molecular arrangement, for example, ChR2 ion channels. Light can then be used to stimulate the neurons. Depending upon a number of factors, such as the location within the brain and the frequency and length of stimulation, different objectives can be achieved. For instance, current techniques for deep brain stimulus (DBS) use electrodes to apply a current directly to the targeted area of the brain. The frequency of the electrical stimulus is sometimes referred to as either low-frequency DBS or high-frequency DBS. Studies have suggested that high-frequency DBS inhibits the generation of impulses from the stimulated cells, while low-frequency DBS facilitates the generation of impulses from the stimulated cells. The frequencies that produce the effects of high-frequency of low-frequency DBS have also been shown to vary depending upon the specific area of the brain being stimulated. According to one example of high-frequency DBS, the neurons are stimulated using electrodes supplying current pulses at frequencies around 100 Hz or more. Such a frequency has been shown to be effective in certain applications, as discussed further herein.

A specific example of DBS is used for the treatment of Parkinson's disease. In this application, DBS is often applied to the globus pallidus interna, or the subthalamic nucleus within a patient's brain. By implanting a biological arrangement that modifies the cells to respond to light, a light flashing light can be used in place of electrodes. Thus, the targeted neuron cells and external electrical signal need not be directly applied to the targeted cells. Moreover, light can often travel from its point of origin farther than electricity, thereby increasing the effective area relative to the stimulation source and only those neurons that have been photosensitized are stimulated.

As with the electrode-based DBS methods, one embodiment of the present invention can be implemented using high-frequency DBS to inhibit neuron generated impulses. While high-frequency DBS has been accomplished at frequencies around 100 Hz, high-frequency DBS using various embodiments of the present invention may not necessarily require the same frequency. For instance, it may be possible to reproduce the inhibiting effects of high-frequency DBS at lower frequencies (e.g., 50 Hz) when using light activated techniques. For example, activation of the halorhodopsin (NpHR) channel intrinsically favors hyperpolarization and resistance to action potential generation. Also, a light-sensitive ion channel may recover more slowly than naturally occurring mammalian ion channels, thus slowing the repolarization (and hence overall reactivity) of a neuron. Thus, various frequencies can be used depending upon the particular application (e.g., the targeted portion of the brain and the desired effect), and the stimulation modality being applied.

Consistent with another example embodiment of the present invention, gene transfer vectors inducing the expression of photosensitive bio-molecules are used to target a specific type of cell. For instance, viral-based proteins (e.g., lentiviruses or retroviruses) can created to target specific types of cells, based upon the proteins that they uniquely express. The targeted cells are then infected by the viral-based gene-transfer proteins, and begin to produce a new type of ion channel (for example ChR2), thereby becoming photosensitive. This can be particularly useful for stimulating the targeted cells without stimulating other cells that are in proximity to the targeted cells. For example, neurons of disparate length, diameter, chronaxie, other membrane properties, electrical insulation, neurotransmitter output, and overall function, lie in close proximity to one another, and thus, can be inadvertently stimulated when using electrodes to provide the stimulation of the neurons. For further details on the generation of viral vectors, reference may be made to U.S. patent application Ser. No. 11/459,636 filed on Jul. 24, 2006, which is fully incorporated herein by reference.

Turning now to the figures, FIG. 1 shows a block diagram of a system for stimulating target cells, according to an example embodiment of the present invention. Block 102 represents a location internal to an organism (e.g., a mammal), as shown by the in vivo designation. Light generator 104 is an implantable device that generates light in vivo. The photosensitive biological portion 106 affects the target cells such that generated light strikes causes stimulation of the target. In one instance, the light generator 104 is a small electronic device on the order of a few millimeters in size. The small size is particularly useful for minimizing the intrusiveness of the device and associated implantation procedure. In another instance, the light generator 104 may include a fiber optic device that can be used to transmit light from an external source to the target cells.

In one embodiment of the present invention, the target cells are modified to contain light-activated ion channel proteins. A specific example of such protein is channelrhodopsin-3 (ChR2), which is a product based upon green alga *Chalamydomanas reinhardtii*.

These light sensitive proteins can be implanted using a number of different methods. Example methods include, but are not limited to, the use of various delivery devices, such as gelatin capsules, liquid injections and the like. Such methods also include the use of stereotactic surgery techniques such as frames or computerized surgical navigation systems to implant or otherwise access areas of the body.

Figure 2:
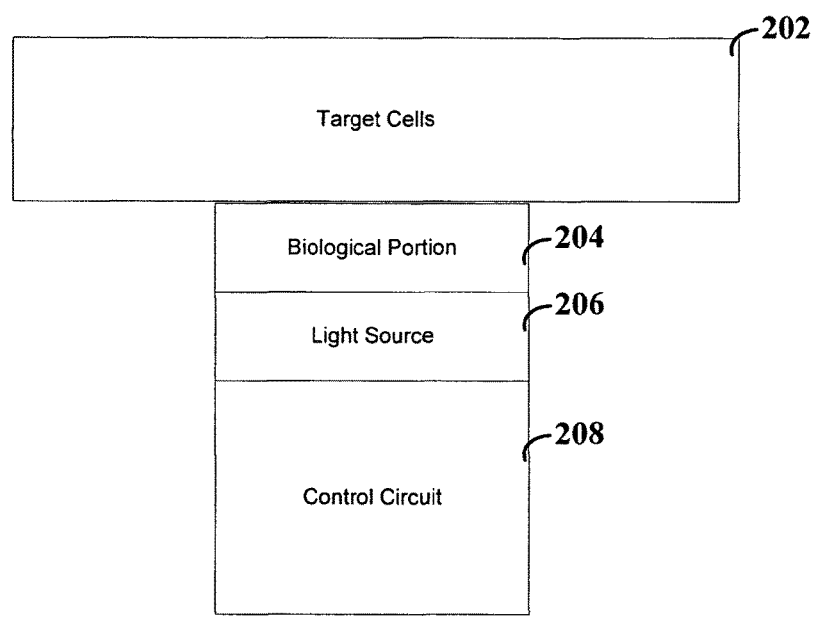
FIG. 2 shows a block diagram of an implantable device for stimulating target cells, according to an example embodiment of the present invention.

FIG. 2 shows a block diagram of an implantable device for stimulating target cells, according to an example embodiment of the present invention. The figure includes control circuit 208, light source 206, biological portion 204 and target cells 202. Biological portion 204 affects the target cells 202 such that the target cells are stimulated in response to light In one embodiment of the present invention, biological portion 204 may be composed of target cells 202 that have been modified to be photosensitive. In another embodiment of the present invention, biological portion 204 may contain biological elements such as gene transfer vectors, which cause target cells 202 to become sensitive to light. An example of this is lentiviruses carrying the gene for ChR2 expression. In this manner, the stimulation of target cells 202 can be controlled by the implantable device. For example, the control circuit 208 can be arranged to respond to an external signal by activating, or deactivating light source 206, or by charging the battery that powers light source 206. In one instance, the external signal is electromagnetic radiation that is received by control circuit 208. For example, radio frequency (RF) signals can be transmitted by an external RF transmitter and received by control circuit 208. In another example, a magnetic field can be used to activate and/or power the control circuit.

Control circuit 208 can be implemented using varying degrees of complexity. In one instance, the circuit is a simple coil that when exposed to a magnetic field generates a current. The current is then used to power light source 206. Such an implementation can be particularly useful for limiting the size and complexity as well as increasing the longevity of the device. In another instance, control circuit 208 can include an RF antenna. Optionally, a battery or similar power source, such as a capacitive element, can be used by control circuit 208. While charged, the power source allows the circuitry to continue to operate without need for concurrent energy delivery from outside the body. This can be particularly useful for providing precise control over the light emitted by light source 206 and for increased intensity of the emitted light.

In one embodiment of the present invention, light source 206 is implemented using a light-emitting-diode (LED). LEDs have been proven to be useful for low power applications and also to have a relatively fast response to electrical signals.

In another embodiment of the present invention, biological portion 204 includes a gelatin or similar substance that contains gene transfer vectors which genetically code the target cells for photosensitivity. In one instance, the vectors are released once implanted into the body. This can be accomplished, for example, by using a containment material that allows the vectors to be released into aqueous solution (e.g., using dehydrated or water soluble materials such as gelatins). The release of the vectors results in the target cells being modified such that they are simulated in response to light from light source 206

In another embodiment of the present invention, the biological portion 204 includes a synthetic mesh that contains the photosensitive cells. In one instance, the cells are neurons that have been modified to be photosensitive. The synthetic mesh can be constructed so as to allow the dendrites and axons to pass through the mess without allowing the entire neuron (e.g., the cell body) to pass. One example of such a mesh has pores that are on the order of 3-7 microns in diameter and is made from polyethylene terephthalate. In another example embodiment, the biological portion 204 includes an injection mechanism as discussed in further detail herein.

Figure 3:
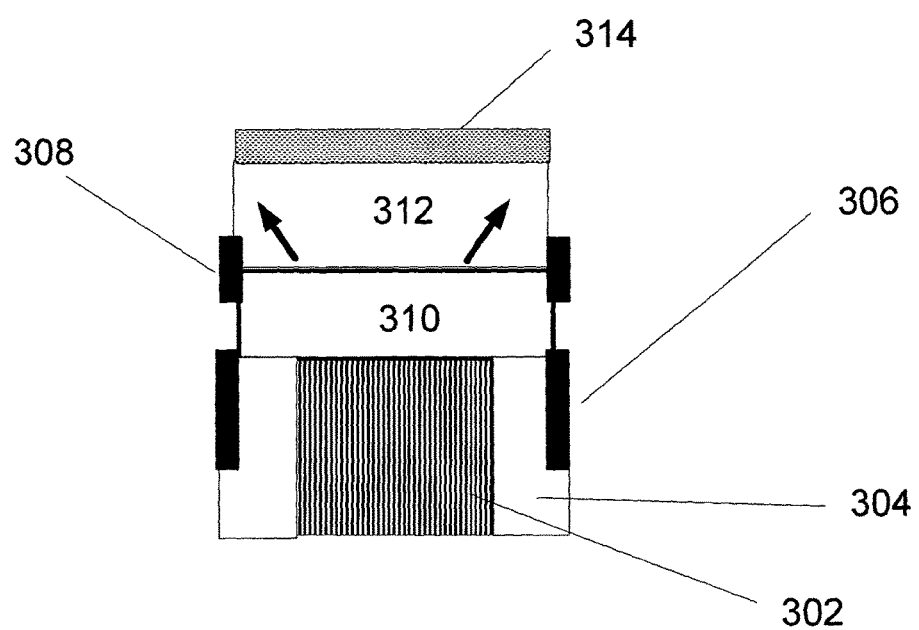
FIG. 3 shows a block diagram of an implantable device, according to an example embodiment of the present invention.

FIG. 3 shows a block diagram of an implantable device, according to an example embodiment of the present invention. The implantable device of FIG. 3 is responsive to a field magnetic. More specifically, an inductor constructed from windings 302 and core 304 generates a current/voltage in response to a magnetic field. The current is passed to control circuit 310 through conductive path 306. In response, control circuit 310 activates light source 312 using conductive path 308. Light source 312 illuminates biological portion 314 in order to stimulate the target cells. In one instance, biological portion 314 includes a gelatin, synthetic mesh or injection mechanism as discussed in further detail herein.

In one embodiment of the present invention, the control portion can be a simple electrical connection, resistive element, or can be removed completely. In such an embodiment, the intensity, duration and frequency of light generated would be directly controlled by the current generated from a magnetic field. This can be particularly useful for creating inexpensive, long lasting and small devices. An example of such an embodiment is discussed further in connection with FIG. 4A and FIG. 4B.

In another embodiment of the present invention, the control portion can be implemented as a more complex circuit. For instance the control circuit may include and otherwise implement different rectifier circuits, batteries, pulse timings, comparator circuits and the like. In a particular example, the control circuit includes an integrated circuit (IC) produced using CMOS or other processes. Integrated circuit technology allows for the use of a large number of circuit elements in a very small area, and thus, a relatively complex control circuit can be implemented for some applications.

In a particular embodiment of the present invention, the inductor (302 and 304) is a surface mount inductor, such as a 100 uH inductor part number CF1008-103K supplied by Gowanda Electronics Corp. The light generating portion is a blue LED, such as LEDs in 0603 or 0805 package sizes. A particular example is a blue surface mount LED having part number SML0805, available from LEDtronics, Inc (Torrance, Calif.). Connective paths 306 and 308 can be implemented using various electrical conductors, such as conductive epoxies, tapes, solder or other adhesive materials. LEDs emitting light in the amber spectrum (as applicable to NpHR channels) are available through commercial sources including this same manufacturer.

Figure 4A:
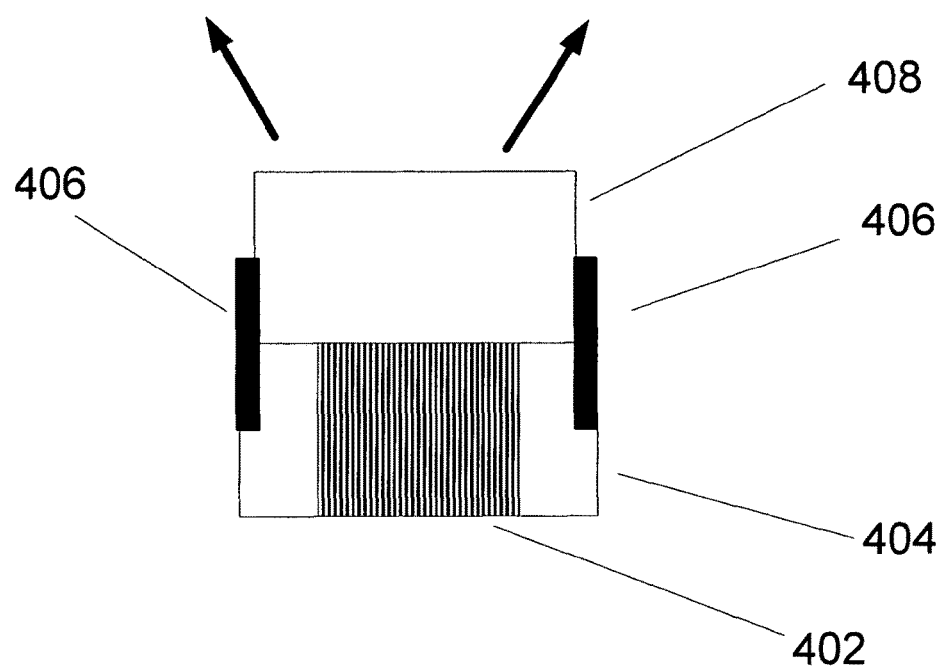
FIG. 4A shows a block diagram of an implantable device, according to an example embodiment of the present invention.
Figure 4B:
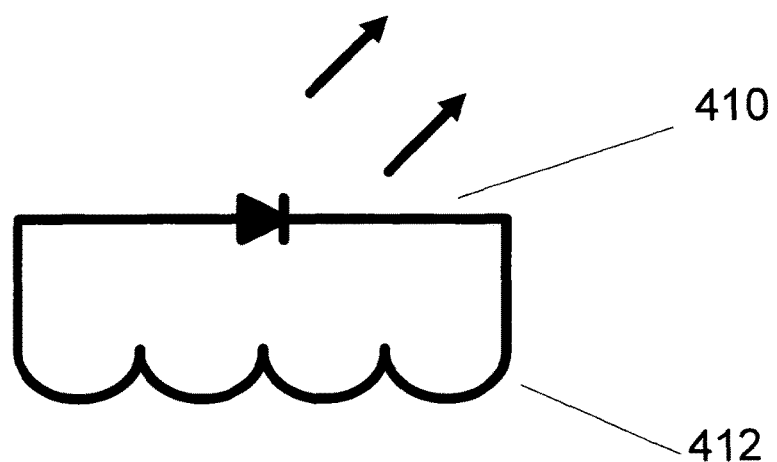
FIG. 4B shows a circuit diagram corresponding to the block diagram of FIG. 4A, according to an example embodiment of the present invention.

FIG. 4A shows a block diagram of an implantable device, according to an example embodiment of the present invention. FIG. 4A shows an inductor comprising coils 402 and core 404 connected to LED 408 using conductive paths shown by 406. FIG. 4B shows a circuit diagram corresponding to the block diagram of FIG. 4A. Inductor 412 is connected in parallel to LED 410. Thus, current and voltage generated by changing a magnetic field seen at inductor 412 causes LED 410 to produce light. The frequency and strength of the changing magnetic field can be varied to produce the desired amount and periodicity of light from LED 410.

Figure 5A:
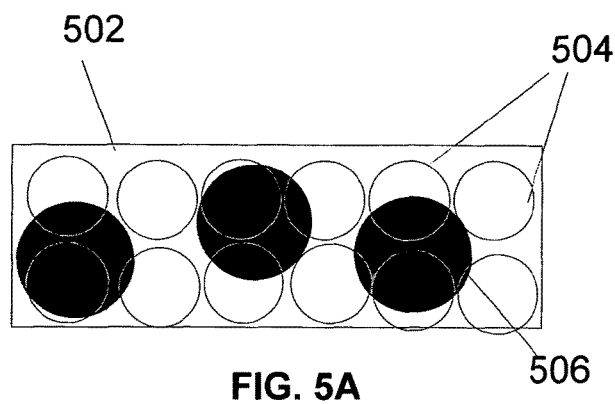
FIG. 5A and FIG. 5B show a diagram of a mesh for containing photosensitive bio-molecules, according to an example embodiment of the present invention.
Figure 5B:
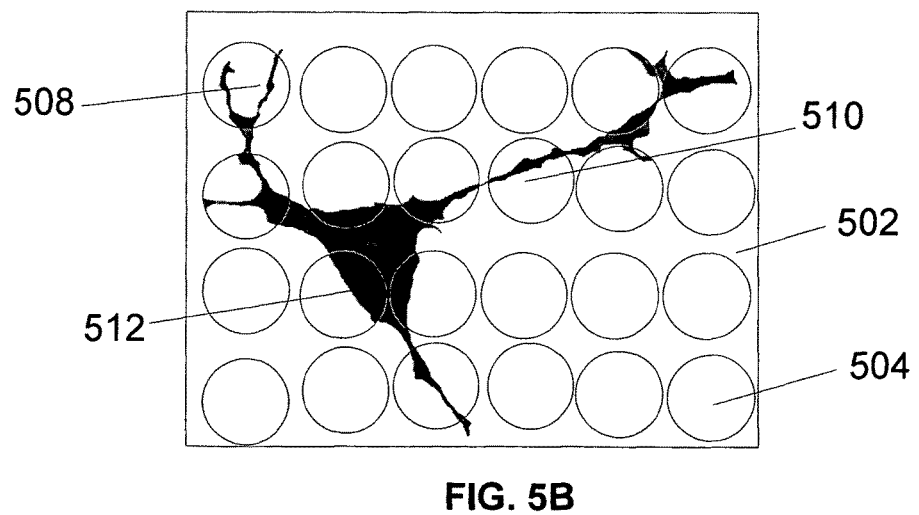

FIG. 5A and FIG. 5B show a diagram of a mesh for containing photosensitive bio-molecules, according to an example embodiment of the present invention. Mesh 502 is constructed having holes 504 of a size that allows illumination to pass but is small enough to prevent cells 506 to pass. This allows for cells 506 to be implanted while still receiving light from a light generator.

In one embodiment of the present invention, the cells 506 are stem cells that are modified to be photosensitive. The stem cells are allowed to mature as shown by FIG. 5B. In a particular instance, the stem cells mature into neurons having a cell body 512, axons/dendrites 508 and 510. The neurons are genetically modified to be photosensitive. Holes 504 are on the order of 3-7 microns in diameter. This size allows some axons and dendrites to pass through holes 504, while preventing the cell body 512 to pass.

Figure 6A:
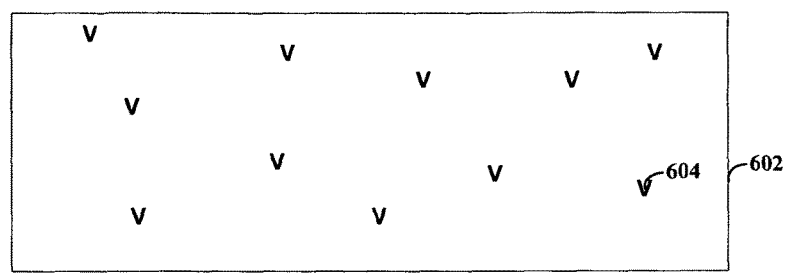
FIG. 6A and FIG. 6B show a diagram of a viral matrix, according to an example embodiment of the present invention.
Figure 6B:
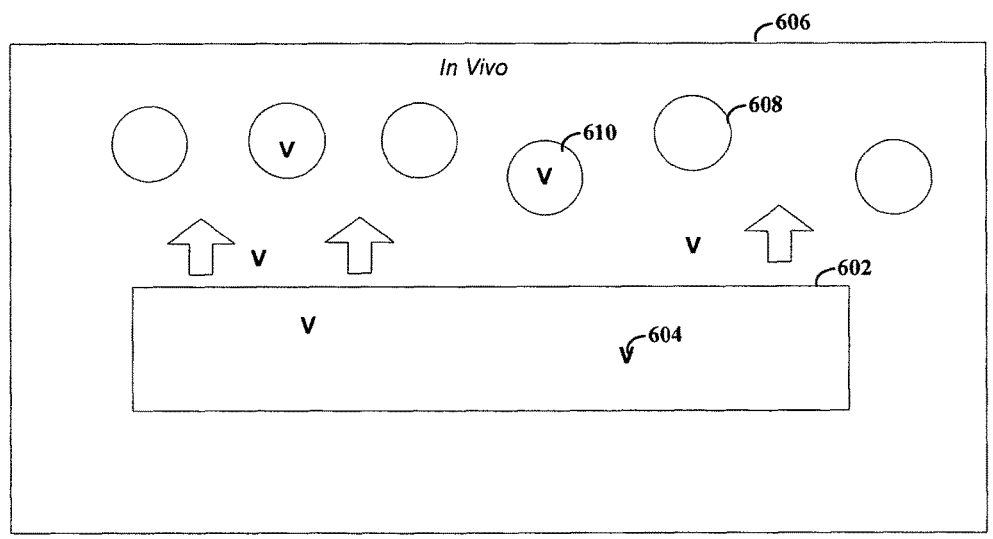

FIG. 6A and FIG. 6B show a diagram of a viral matrix, according to an example embodiment of the present invention. The viral matrix includes structure 602, which contains viral vectors 604. In one instance, structure 602 includes a gel or fluid substance that contains viral vectors 604 until they are implanted in a mammal 606. Once viral vectors 604 are released, they infect target cells 608 in the vicinity of the implanted viral matrix as shown by FIG. 6B. Infected target cell 610 becomes photosensitive, and thus, light can be used to control the stimulation of target cell 610.

According to one embodiment of the present invention, structure 602 is a gelatin that has been impregnated, or otherwise sealed with viral vectors 604 contained within the gelatin. When structure 602 is implanted, the gelatin is hydrated and or dissolved, thereby releasing viral vectors 604. Standard commercially available gelatin mix may be used, in addition to compounds such as Matrigel by BD Biosciences division of Becton Dickenson and Company (Franklin Lakes, N.J.)

Figure 7:
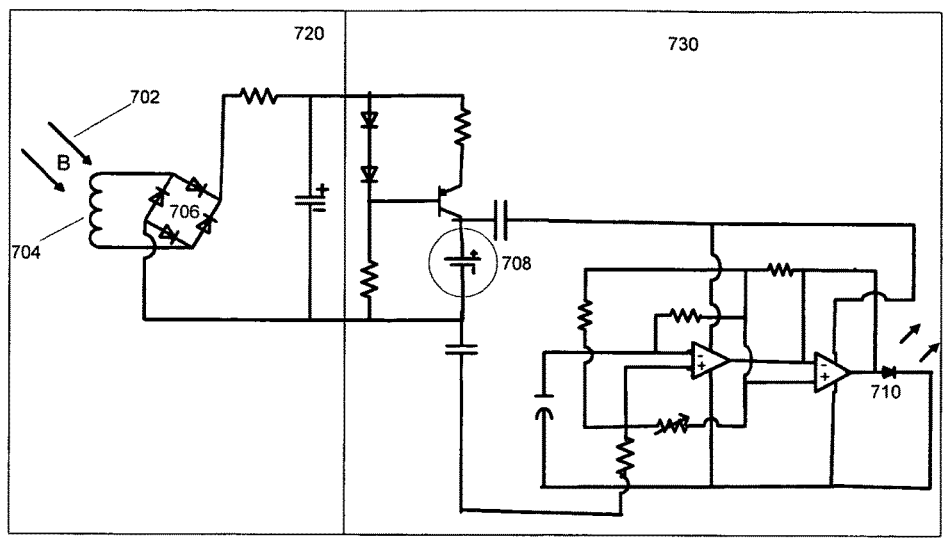
FIG. 7 shows a circuit diagram of a circuit that produces light in response to a magnetic field, according to an example embodiment of the present invention.

FIG. 7 shows a circuit diagram of a circuit that produces light in response to a magnetic field, according to an example embodiment of the present invention. FIG. 7 includes an input circuit 720 and an output circuit 730. Inductor 704 generates current in response to magnetic field 702. Due to properties of magnetic fields, the current produced by inductor 704 is an alternating current (AC) signal. Full-wave bridge rectifier 706 rectifies the AC signal and along with an RC circuit generates a relatively stable voltage from the AC signal. This generated voltage is responsive to magnetic field 702 and output circuit 730 generates light when the generated voltage is at a sufficient level. More specifically, power from battery 708 is used to drive LED 710 in response to magnetic field 702. This is particularly useful for applications where the magnetic field 702 seen by inductor 704 is less powerful (e.g., due to the in vivo location of inductor 704).

Figure 8A:
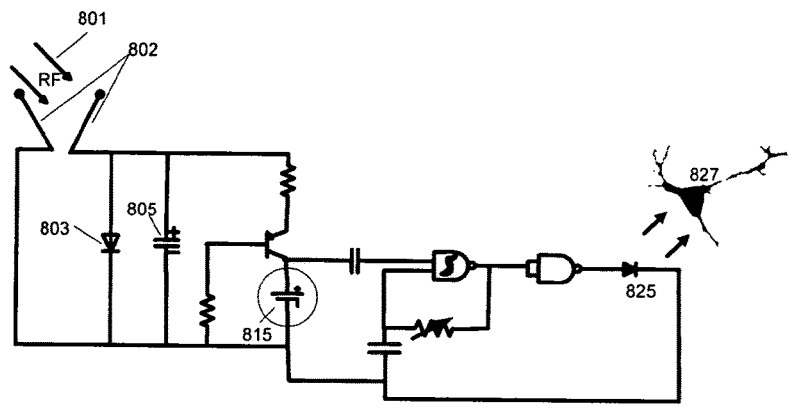
FIG. 8A-8C show a block diagram and circuits for the production of light in response to a RF signal, according to an example embodiment of the present invention.

FIG. 8A shows a circuit diagram of a circuit that produces light in response to RF signal 801, according to an example embodiment of the present invention. Antenna 802 is used to receive RF transmission 801 and convert the signal to electricity. The received transmission is rectified by diode 803 and further filtered by capacitor 805. In a one instance, diode 803 can be implemented using a diode having a low forward bias and fast switching capabilities, such as a Schottky diode.

In a particular embodiment of the present invention, RF transmission 801 contains a power component for charging battery 815 and a signal component for controlling LED 825. Capacitor 805 can be selected to separate these components for use by the circuit. For instance, the power component may be a relatively low-frequency, large-amplitude signal, while the signal component is a relatively high-frequency, small-amplitude signal. Capacitor 805 can be selected to filter the power component of the signal to create a corresponding voltage. The remaining the high-frequency component of the RF transmission is added to this voltage. The power component of the transmission can then be used to charge on the battery 815, and the signal component of the transmission is used to enable LED 825. The light generated by LED 825 to triggers stimulus of the target cells 827.

Figure 8B:
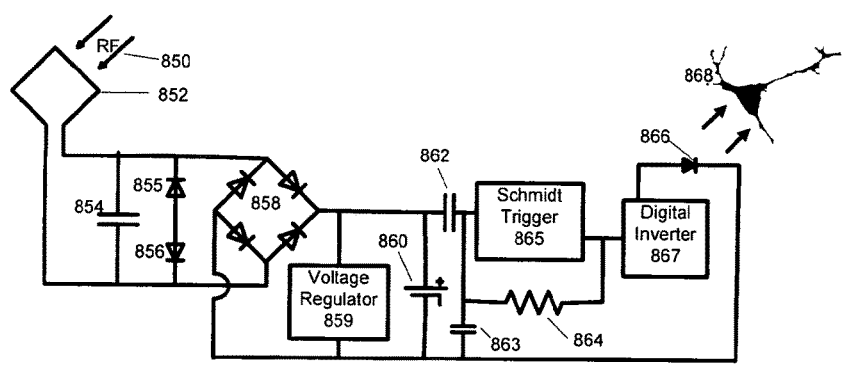

FIG. 8B illustrates an alternative embodiment radio-frequency energy accumulator, which charges a battery, which in turn, powers a digital pulse generator, which powers a LED. An electromagnetic signal 850 is received by loop antenna 852 generating a corresponding electrical signal. The voltage generated from loop antenna 852 is limited by the reverse bias voltage of the diodes 855 and 856 and stored in capacitor 854. In a particular instance these diodes have a low reverse bias voltage that is relatively precise, such as a Zener diode. Electromagnetic signal 850 is rectified via diode rectifier bridge 858 and filtered by voltage regulator 859 to produce a DC voltage. The DC can be used to charge power source 860.

Battery 860 is coupled to the input of Schmidt trigger 865 through capacitor 862. Feedback from the output of the Schmidt trigger is provided through resistor 864 relative to the charge on capacitor 863. Accordingly, the frequency of the square-wave output of Schmidt trigger 865 is determined by the values of the resistor-capacitor network including capacitor 863 and resistor 864. Resistor 864 and capacitor 863 may be fixed or variable. The output of Schmidt trigger 865 is fed through digital inverter 867 which powers LED 866. Light from LED 866 is transmitted to light-sensitive neurons 868 relative to the frequency of the square-wave output of Schmidt trigger 865.

Figure 8C:
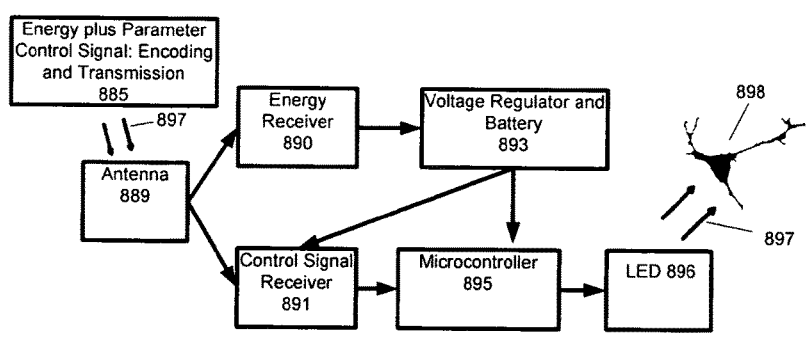

FIG. 8C illustrates block diagram for an electromagnetic filed (EMF) energy accumulator and pulsing approach in which the received EMF 897 (for example radiofrequency energy) includes not only energy for accumulation, but also an encoded signal regarding instructions to microcontroller 895. In step 885 (Energy plus Parameter Control Signal: Encoding and transmission), a control instruction signal is encoded to ride upon the energy component by methods known in the art, for example, by frequency modulation. Energy receiver block 890 uses a portion of the EMF signal to provide power to block 893. Control signal receiver block 891 uses a portion of the EMF signal to provide control instructions to microcontroller block 895.

The control instruction can be used to transmit information regarding the various parameters of the generated light, such as frequency, strength, duration, color, and the like. These instructions can be decoded and processed using a microcontroller or logic circuitry as shown by block 895. Block 895 can generate control signal(s) in response to the decoded instructions. Accordingly, the frequency (and other parameters) of the light generated by LED 896 rate need not be fixed for the given implanted device. Antenna 889 delivers input to the Energy Receiver 890 (providing power to voltage regulator and battery circuitry 893). Concurrently, antenna 889 delivers encoded data to Control Signal Receiver 891, which provides control input to microcontroller 895 that drives LED 896. Selected wavelength light 897 is then delivered to electrically excitable cell 898. The battery in the voltage regulator and battery circuitry 893 provides power to the microcontroller 895 and the Control Signal Receiver 891.

The circuit diagrams of FIG. 7 and FIGS. 8A, 8B and 8C are merely illustrative of a few particular embodiments of the present invention, and various other implementations are envisioned. For example, particular embodiments implement a light source that uses a blue LED; however, other colors and light sources can be implemented depending upon the particular application.

Figure 9A:
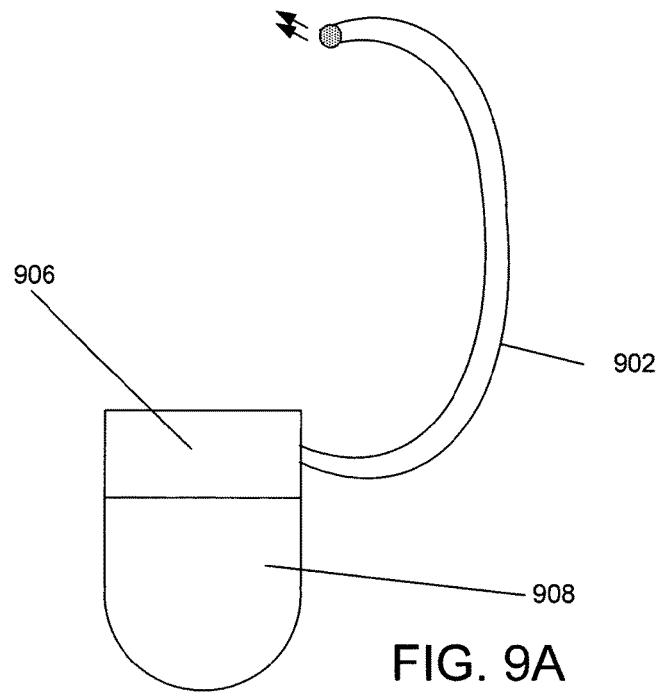
FIG. 9A and FIG. 9B each show a diagram of a fiber-optic device, according to an example embodiment of the present invention.
Figure 9B:
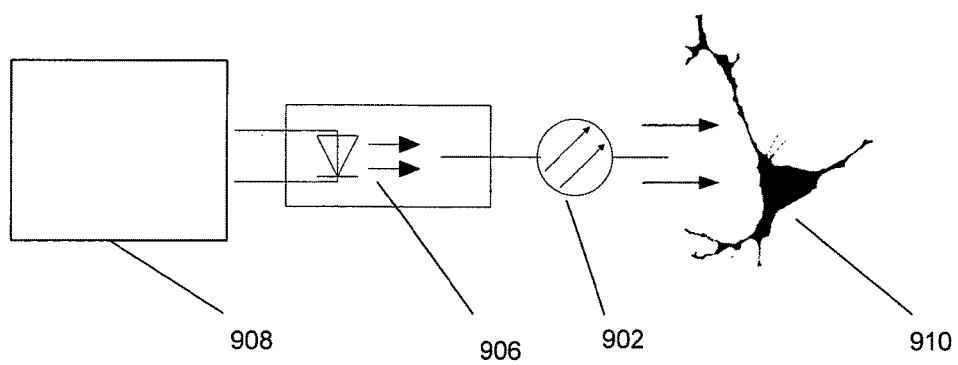

FIG. 9A and FIG. 9B each show a diagram of a fiber-optic device, according to an example embodiment of the present invention. The fiber-optic device includes a control portion 908, a light generator 906 and a fiber optic cable 902.

Fiber optic cable 902 can be positioned near a photosensitive biological portion, such as a viral matrix or synthetic mesh as discussed herein. This allows for control portion 908 and light generator 906 to be located at a distance from the target cells 910 (e.g., at a distance corresponding to the length of fiber-optic cable 902). This can be particularly useful for minimizing the size of the portion of the implanted device that is near the target cells, for example, where the target cells are located at or near a sensitive location within the brain. In some instances, the remote location of portions 908 and 906 also facilitates modifications of the device, including, but not limited to, replacement of various components (e.g., batteries), changes in stimulation frequency and length.

Control portion 908 can be configured to respond to an external signal, such as magnetic field or RF signals. Alternatively, control portion 908 can be configured to enable light generator 906 according to a programmed schedule or a combination of an external signal and a programmed response.

Figure 10A:
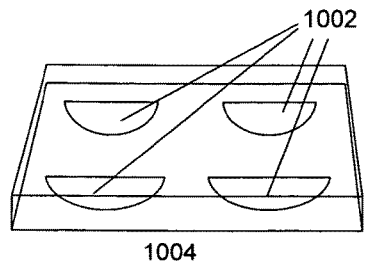
FIGS. 10A-10D depict various stages in the production of a photosensitive biological portion, according to an example embodiment of the present invention.

FIGS. 10A-10D depict various stages in the production of a photosensitive biological portion, according to an example embodiment of the present invention. More specifically, FIG. 10A shows molding structure 1004 having several molds 1002. Molds 1002 are constructed to various sizes depending upon the particular application. In one such application, the molds are a few millimeters or less in diameter.

Figure 10B:
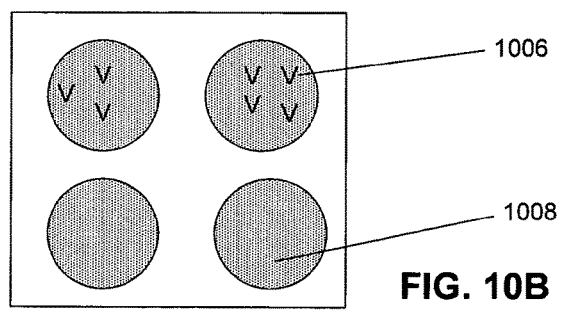

FIG. 10B shows the molds 1002 from FIG. 10A after applying a layer of gelatin or similar substance as shown by 1006 and 1008. Moreover, viral vectors (shown by 'v') are in the upper two molds. These viruses may be suspended within media 1012, which may be a liquid or gelatinous media. Such liquids include normal saline, HEPES-buffered saline and other known viral sustenance and transfer media. Suitable gelatinous media includes Matrigel (BD Biosciences, San Jose Calif.) These viral vectors are designed transfer genes for light-sensitization to the membranes of targeted cells after implantation.

Figure 10C:
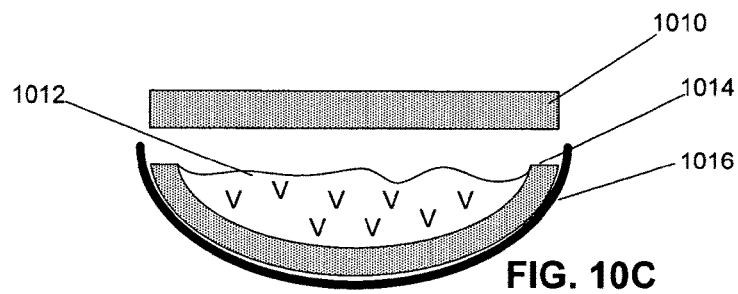

FIG. 10C shows a side view of mold 1006. 1016 represents the molding structure that forms the shape of gelatin layer 1014. Gelatin layer 1014 traps viral vectors contained within media 1012. A top gelatin layer 1010 is applied to fully contain the viral vectors.

Figure 10D:
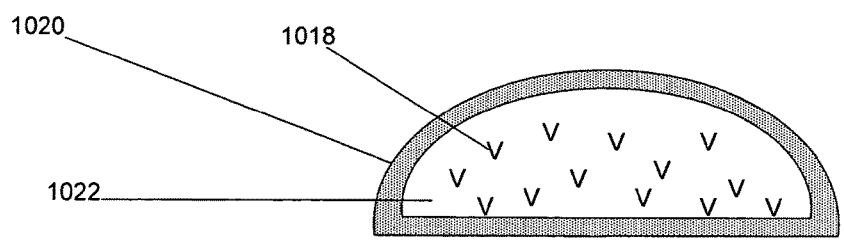

FIG. 10D shows the resulting viral vector capsule. The viral vectors 1018 are contained within area 1022 by casing 1020. Casing 1020 can be designed to dissolve or otherwise allow viral vectors 1018 to disseminate towards the target cells once implanted. In one instance, the capsule is constructed of a water soluble material, for example, gelatin, so that upon implantation the viral vectors are allowed to escape into the body. Water soluble capsule materials are well known in the pharmaceutical industry.

Figure 11:
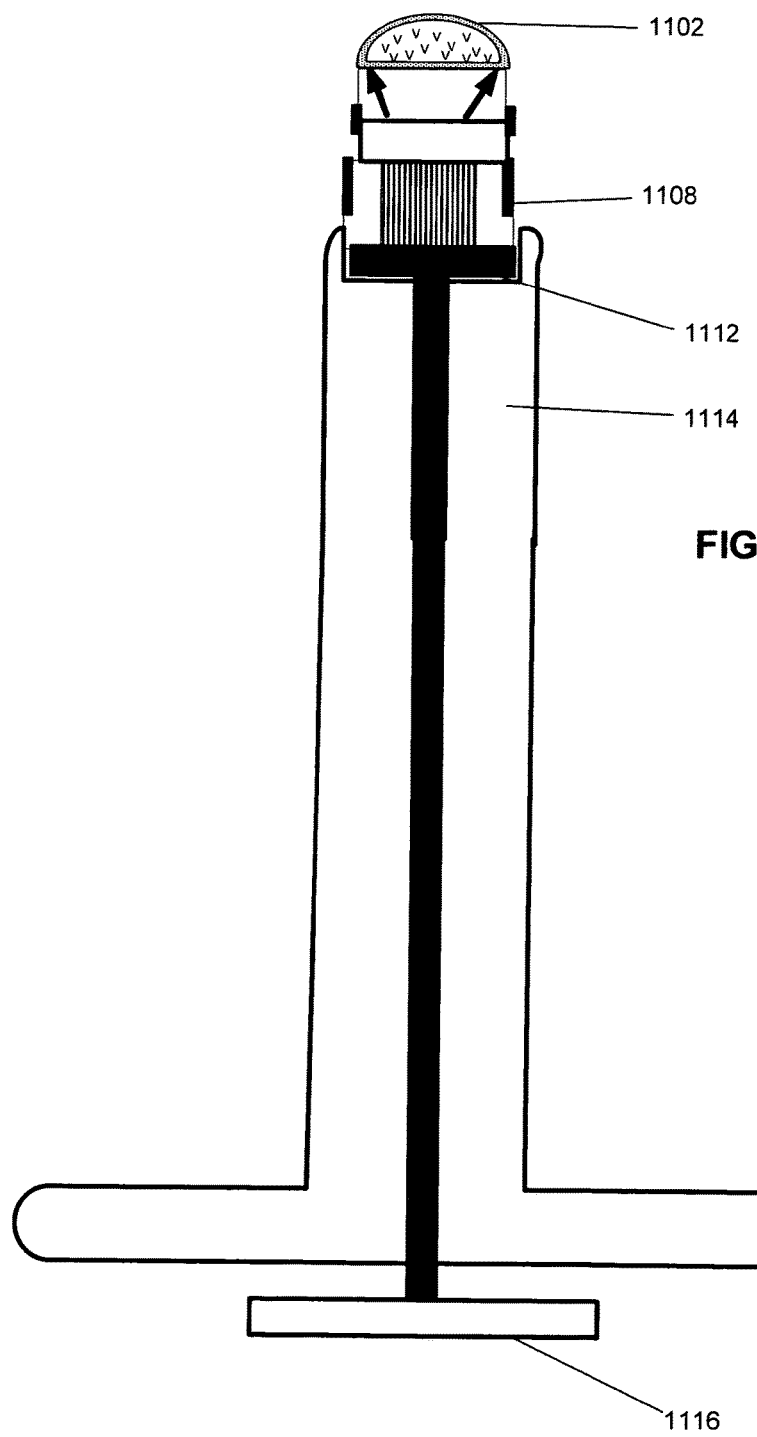
FIG. 11 shows an implantation device, according to an example embodiment of the present invention.

FIG. 11 shows an implantation device, according to an example embodiment of the present invention. Biological portion 1102 and light generation device 1108 are implanted using the implantation device. For example, the shaft of the device 1114 is positioned near the target cells. Next, a user of the device presses on portion 1116 which causes portion 1112 to place biological portion 1102 and light generation device 1108 near the target cells. The implantation device can then be removed.

Figure 12A:
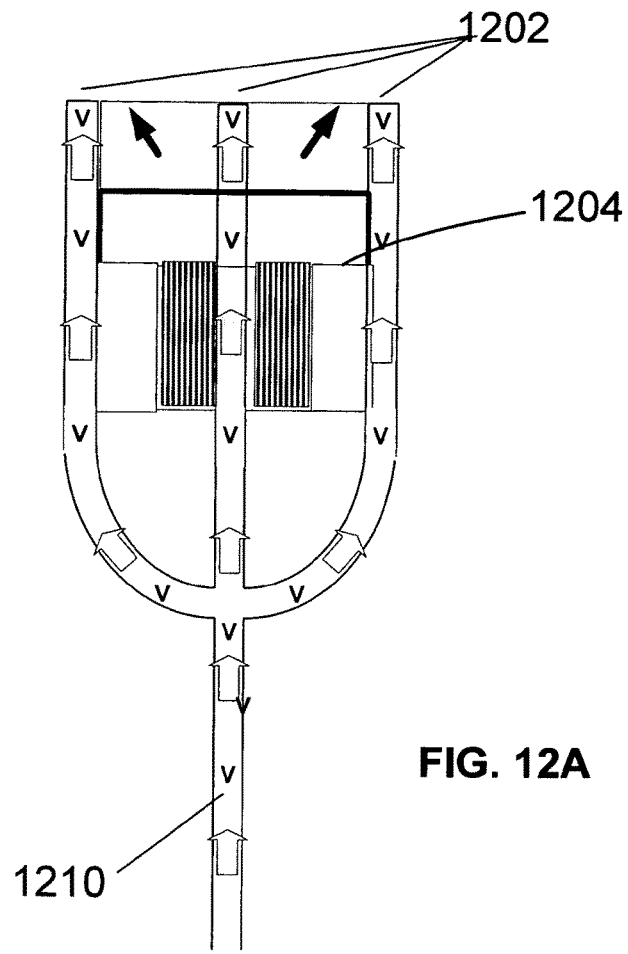
FIG. 12A and FIG. 12B show a diagram for another implantation device, according to an example embodiment of the present invention.
Figure 12B:
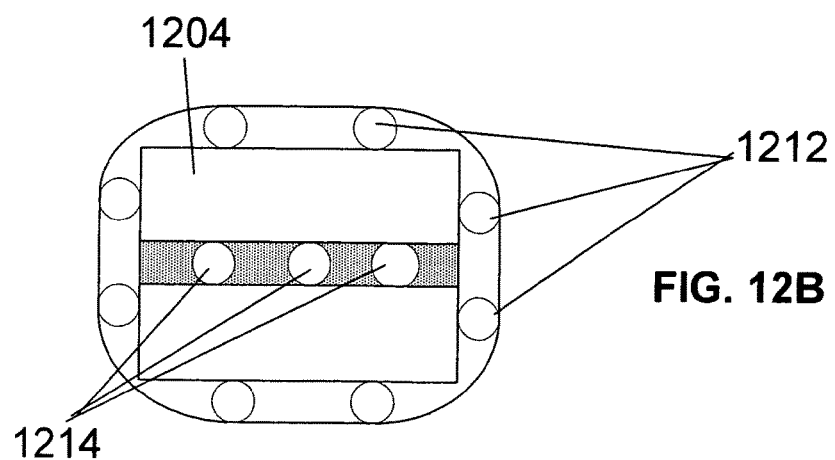

FIG. 12A and FIG. 12B show a diagram for another implantation device, according to an example embodiment of the present invention. Implantable light generating device 1204 is surrounded by, and permeated by fluid channels 1202. Fluid channels 1202 allow a solution 1210 containing bio-molecular material (e.g., photosensitizing viral vectors) to be injected immediately proximal to light generating device 1204 and the target cells. The fluid channels can be located outside of device 1204 and/or within device 1204, as shown by 1212 and 1214 respectively. In this manner, the viral vectors can be injected in large quantities or over a period of time. For instance, cells infected by viral vectors can revert back to their pre-infection state after a period of time. Using the device of FIG. 12A, the viral vectors can be periodically reintroduced to the target cells. Alternatively, different viral vectors can be introduced through the fluid channels, allowing for targeting of different cells at the implantation site. This can be particularly useful for staged treatment through stimulation of different types of cells.

A specific embodiment of the present invention relates to a method for genetically modifying neurons to express light-sensitive ion channel ChannelRhodopsin (ChR2). In this method, pulses of blue light causes ChR2 neurons to fire action potentials corresponding to each pulse. Depolarization and repolarization occur on a millisecond timescale making this method consistent with normal network neurophysiology.

Specific targeted neurons are modified using viral vectors for gene transfer. For further details on the generation of viral vectors reference can be made to Boyden et al 2005, Zhang et al 2006, both of which are fully incorporated herein by reference. This transfection results in the introduction of a gene for a single protein, a cell membrane ion channel, known as "Channelrhodopsin 2", or "ChR2". In nature, ChR2 resides on the cellular membrane of unicellular green algae *Chlamydormas reinhardtii*. Upon absorption of blue light (470-480 nm), this ion channel briefly opens, allowing cation influx. When transfected into a mammalian nerve cell, affected nerves become photosensitive, producing light-triggered action potentials. To produce this action potential, photosensitized nerves appear to require 5-10 mW/mm of blue light intensity, in flashes up to 30 Hz. In experimental conditions, 98% of the time, such a flash of light produces an action potential within 50 μseconds of the flash, with a variability (jitter) of 5 μseconds.

A neuronal-type specific feature which is also a robust promoter (for example, CaMKIIα) is inserted adjacent to the ChR2 code within the virus, and the line is propagated by calcium-phosphate cotransfection of 293FT cells. The supernatant is then cetrofuged into viral pellets, which are placed within phosphate-buffered saline.

In a particular instance, application of an algal light-gated ion channel Channelrhodopsin-2 is used for photostimulation. The first 315 amino-acid residues of the algal Channelrhodopsin-2 (abbreviated as ChR2 when coupled with retinal, or Chop-2 for the gene) from *Chlamydomonas reinhardtii* can be used to impart fast photosensitivity upon mammalian nerve cells, by using a viral vector to insert the gene for ChR2 into targeted nerve cells which may subsequently express this gene. ChR2 is a seven-transmembrane protein with a molecule of all-trans retinal (ATR) bound at the core as a photosensor. Upon illumination with approximately 470 nm blue light, ATR isomerizes and triggers a conformational change to open the channel pore. As ChR2 is a light-sensitive ion channel, it allows an inward current to be evoked within 50 μs of illumination. Combining ChR2 with ultrafast light switching it is possible to activate neurons at the temporal precision of single action potentials, reliably over sustained multiple action potential trains.

In another instance, application of bacterial light-gated chloride channel halorhodopsin (NpHR) is used for photostimulation. This ion channel can be imparted upon mammalian nerve cells by using a viral vector to insert the gene for NpHR into targeted nerve cells, which may subsequently express this gene. Upon illumination with approximately 550 to 626 nm amber light, active pumping of chloride ions into the neuronal cytoplasm results in hyperpolarization of the cell.

For each application, the underlying physical properties of the native signal can be considered when choosing the most suitable of these described photostimulation methods. Excitable cells distinguish inputs in part based on their temporal properties, channel recruitment patterns and amplitude or polarity characteristics. Regarding temporal properties, glutamate uncaging and ChR2 achieve responses on the millisecond time scale. Such responses are well suited for photostimulating pathways triggered by fast synaptic events and action potentials. Regarding channel recruitment patterns, glutamate uncaging directly activates native glutamate receptors and so may achieve physiological spatial patterns of subcellular excitation. However, the other photostimulation methods, via depolarization, will recruit native voltage-activated channels such as voltage-dependent calcium, sodium and potassium channels, and thereby activate native, spatially sensitive signaling pathways. With such methods, channels could be activated experimentally so that populations can be labeled via stereotactic injection of viruses that effect retrograde axonal transport, by taking advantage of region specific axonal projections. Just as with ChR2, other genetically based photostimulation methods (including NpHR) can use these targeting strategies, although some multicomponent systems may be difficult to implement without the use of transgenic technologies. For a photostimulation-based method, sufficient gene expression must be achieved to elicit physiologically relevant levels of current.

In a particular instance, ChR2 is activated with blue light (excitation around 470 nm). Successful photostimulation of ChR2-expressing cells requires at least 5 mW/mm2 of blue light to reach the sample.

ChR2 has been estimated to possess a single-channel conductance as low as 50 femtosiemens. This would imply that between 100,000 and 1,000,000 ChR2 molecules would have to be generated and localized to the neuronal membrane to achieve the observed currents in the range of 1 nA (starting from a resting potential of −70 mV and neglecting space-clamp issues and changes in driving force due to ion entry).

Since sensitivity to blue light via ChR2 is induced when a viral vector inserts the ChR2 gene into a previously normal cell, the insertion may be genetically targeted to the products expressed by specific cellular subtypes. For example, it might be advantageous to cause only dopaminergic neurons, and not cholinergic neurons to react to blue light.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims.

What is claimed is:

1. A method for stimulating a target mammalian neural cell, the method comprising:
    a) implanting a light-emitting device near the target neural cell, wherein device comprises a containment material that comprises a nucleic acid comprising a nucleotide sequence encoding a light-responsive opsin polypeptide, wherein the nucleic acid is released from the light-emitting device and enters the target neural cell, and wherein the light-responsive opsin polypeptide: i) is a channelrhodopsin comprising an amino acid having at least 95% amino acid sequence identity to SEQ ID NO:1; or ii) is a halorhodopsin; and
    b) activating the light-emitting device to emit light, thereby activating the light-responsive opsin polypeptide and stimulating the target neural cell.

2. The method of claim 1, wherein the light-emitting device is stereotactically deliverable.

3. The method of claim 1, wherein the light-emitting device is scopically deliverable.

4. The method of claim 1, wherein the light-emitting device comprises a light-emitting diode.

5. The method of claim 1, wherein the light-emitting device comprises a light generator, and a signal-reception circuit coupled to the light generator, and wherein the method comprises activating the light-emitting device in response to an external signal.

6. The method of claim 5, wherein the external signal is an electromagnetic transmission, and wherein the signal-receptor circuit comprises at least one coil and a light-emitting diode, said at least one coil and the light-emitting diode being activated to generate light in response to the electromagnetic transmission.

7. The method of claim 5, wherein the external signal is a radio frequency (RF) transmission, and wherein the signal-receptor circuit comprises an RF receiver, wherein the RF receiver is activated to generate light in response to the RF transmission.

8. The method of claim 6, wherein the electromagnetic transmission comprises a power portion of the transmission that charges a power source and a signal portion of the transmission that enables or disables the light generator.

9. The method of claim 1, wherein the nucleic acid is contained within a matrix.

10. The method of claim 9, wherein the matrix comprises gelatin.

11. The method of claim 1, wherein the nucleic acid is a viral vector.

12. The method of claim 11, wherein the viral vector is contained within a matrix.

13. The method of claim 1, wherein the light-responsive opsin polypeptide has at least 95% amino acid sequence identity to SEQ ID NO:1.

* * * * *